US008049063B2

(12) United States Patent  
Tu et al.

(10) Patent No.: US 8,049,063 B2  
(45) Date of Patent: Nov. 1, 2011

(54) RICE BENTAZON AND SULFONYLUREA HERBICIDE RESISTANT GENE CYP81A6

(75) Inventors: Jumin Tu, Hangzhou (CN); Jiwen Zhang, Wuhan (CN); Gang Pan, Hangzhou (CN); Xianyin Zhang, Hangzhou (CN); Xiaozhi Wu, Wuhan (CN)

(73) Assignees: Zhejiang University, Hangzhou (CN); Wuhan Fortune Science and Technology Co., Ltd., Wuhun (CN)

( * ) Notice: Subject to any disclaimer, the term of this patent is extended or adjusted under 35 U.S.C. 154(b) by 450 days.

(21) Appl. No.: 11/993,990

(22) PCT Filed: Jun. 28, 2005

(86) PCT No.: PCT/CN2005/000936  
§ 371 (c)(1),  
(2), (4) Date: Jul. 21, 2008

(87) PCT Pub. No.: WO2007/000077  
PCT Pub. Date: Jan. 4, 2007

(65) Prior Publication Data  
US 2008/0313772 A1 Dec. 18, 2008

(51) Int. Cl.  
*A01H 5/00* (2006.01)  
*A01H 1/00* (2006.01)  
*C07H 21/04* (2006.01)

(52) U.S. Cl. ........ 800/278; 800/286; 800/298; 800/300; 435/410; 435/418; 435/320.1; 536/23.6

(58) Field of Classification Search .................... None  
See application file for complete search history.

(56) References Cited

U.S. PATENT DOCUMENTS

| 6,380,465 B1 | 4/2002 | Barrett |
| 6,768,043 B2 | 7/2004 | Chory et al. |
| 2006/0123505 A1* | 6/2006 | Kikuchi et al. ............ 800/278 |

FOREIGN PATENT DOCUMENTS

| CN | 1152029 | 6/1997 |
| CN | 1415623 | 5/2003 |
| WO | WO-9919493 | 4/1999 |
| WO | WO-03076633 | 9/2003 |

OTHER PUBLICATIONS

Database GenEmbl, Accession No. AC084282, Apr. 20, 2002.*  
Bode et al., "Biotransformation of atrazine in transgenic tobacco cell culture expressing human P450," *Pest Management Science* vol. 60, 49-58 (2003).  
Deng et al., "Characterization of cytochrome P450-mediated bensulfuron-methyl O-demethylation in rice" *Pesticide Biochem. & Physiology* vol. 74, 102-115 (2003).  
Didierjean et al.,"Engineering Herbicide Metabolism in Tobacco and Arabidopsis with CYP76B1, a Cytochrome P450 Enzyme from Jerusalem Artichoke," *Plant Physiology*, vol. 130, 179-189 (2002).

Feldmann, "Cytochrome P450s as genes for crop improvement," *Current Opinion in Plant Biology*, vol. 4, 162-167 (2001).  
GeneBank:Apr. 20, 2002 Accession No. AC084282.6 GI: 14389338.  
GeneBank:Nov. 9, 2004 Accession No. XP_469850 GI: 50918907.  
International Search Report in PCT/CN2005/000936 dated Apr. 6, 2006.  
Inui et al., "Herbicide Metabolism and Tolerance in the Transgenic Rice Plants Expressing Human CYP2C9 and CYP2C19," *Pesticide Biochem. & Physiology* vol. 71, 156-169 (2001).  
Inui, et al. "Herbicide resistance in transgenic plants with mammalian P450 monooxygenase genes," *Pest Management Sci.*, vol. 61, 268-291 (2005).  
Liu et al., Molecular Mapping for Bentazon Susceptible lethality gene in rice cultivar Nonrin 8m, *J. of Nanjing Agri. Univ*, vol. 27, 17-19.  
Ohkawa et al., "Molecular Mechanism of Herbicide Resistance with Special Emphasis On Cytochrome P450 Monooxgenase," *Plant Biotechnology* vol. 15, 173-176 (1998).  
Ohkawa et al., "The use of cytochrome P450 genes to introduce herbicide tolerance in crops: a review" *Pesticide Science*, vol. 55, 867-874 (1999).  
O'Keefe et al., "Plant Expression of a Bacterial Cytochrome P450 That Catalyzes Activation of a Sulfonylurea Pro-Herbicide," *Plant Physiol.* vol. 105, 473-482 (1994).  
Persans et al., "Differential Induction of Cytochrome P450-Mediated Triasulfuron Metabolism by Naphthalic Anhydride and Triasulfuron," *Plant Physiol.*, vol. 109, 1483-1490 (1995).  
Robineau et al., "The Chemically Inducible Plant Cytochrome P450 CYP76B1 Actively Metabolizes Phenylureas and Other Xenobiotics," *Plant Physiology* vol. 118, 1049-1056 (1998).  
Schuler et al., "Functional genoimics of P450s," *Annu. Rev. Plant Biol.* vol. 54, 629-67 (2003).  
Shiota et al., "Herbicide-Resistant Tobacco Plants Expressing the Fused Enzyme between Rat Cytochrome P4501A1 (CYP1 AI) and Yeast NADPH-Cytochrome P450 Oxidoreductase," *Plant Physiology*, vol. 106, 17-23 (1994).  
Siminszky et al., "Expression of a soybean cytochrome P450 monooxygenase cDNA in yeast and tobacco enhances the metabolism of phenylurea herbicides" *PNAS* vol. 96, 1750-1755 (1999).  
Wensheng et al., "Cytochrome P450 Monooxygenase Immobilization as a Model of Herbicide Metabolism in vitro," *High Technology Letters* 9-12.  
Wensheng et al., "Metabolism of herbicide by plant Cytochrome P450," *J. Northeast Agri. Univ.* vol. 28, 201-208 (1997).  
Werck-Reichhart et al., "Cytochromes P450," *The Arabdopsis Book* 1-28.  
Werck-Reichhart et al., "Cytochromes P450 for engineering herbicide tolerance," *Trends in Plant Science*, vol. 5, 116-123 (2000).

(Continued)

*Primary Examiner* — Eileen B O Hara  
(74) *Attorney, Agent, or Firm* — Marshall, Gerstein & Borun LLP

(57) ABSTRACT

The present invention provides a kind of rice endogenous bentazon and sulfonylurea herbicide resistant gene (Cyp81A6 gene), and its functional conservative variants, the biological activity subfragments or derivatives with the same function. It also provides a kind of method to prevent the selling mixtures during hybrid seed production. It also provides the novel means of the directional genetic manipulation and the improvement of biological traits.

12 Claims, 11 Drawing Sheets

OTHER PUBLICATIONS

Yamada et al., "Enhancement of metabolizing herbicides in young tubers of transgenic potato plants with the rat CYP1A1 gene," *Theor Appl Genet* vol. 105, 515-520 (2002).

Yamada et al. "Inducible cross-tolerance to herbicides in transgenic potato plants with the rat CYP1A1 gene," *Theor Appl Genet* vol. 104, 308-314 (2002).

Yamada et al., "Molecular Cloning of Novel Cytochrome P450 Species Induced by Chemical Treatments in Cultured Tobacco Cells," *Pesticide Biochem & Physiology*, vol. 68, 11-25 (2000).

Zhang et al., "A bentazon and sulfonylurea sensitive mutant: breeding, genetics and potential application in seed production of hybrid rice," *Theor. Appl. Genet*. vol. 105, 16-22 (2002).

Zhu, et al. "Engineering herbicide-resistant maize using chimeric RNA/DNA Oligionucleotides" *Nature/Biotech*, vol. 18,555-558 (2000).

European Search Report in EP 05 75 7223 dated Mar. 10, 2009.

Genbank Accession No. AC084282, Apr. 20, 2002.

Genbank Accession No. ADJ11798, May 20, 2004.

Genbank Accession No. AK104825, Jul. 19, 2003.

Genbank Accession No. Q94HA5, Dec. 1, 2001.

Pan et al., Plant Mol. Biol., 61:933-943 (2006).

Barcelo et al., Transgenic cereal (tritordeum) plants obtained at high efficiency by microprojectile bombardment of inflorescence tissue, Plant J., 5:583-92 (1994).

Breitler et al., Efficient microprojectile bombardment-mediated transformation of rice using gene cassettes, Theor. Appl. Genetics, 104:709-19 (2002).

Cai et al., Aberrant splicing of intron 1 leads to the heterogeneous 5' UTR and decreased expression of waxy gene in rice cultivars of intermediate amylose content, Plant J., 14:459-65 (1998).

Chen et at, Acta Phytophysiologica Sinica, 27:381-6 (2001). [Chinese only].

Elbashir et al., RNA interference is mediated by 21- and 22-nucleotide RNAs, Genes Dev., 15:188-200 (2001).

Frances et al., Use of alternate splice sites in granule-bound starch synthase mRNA from low-amylose rice varieties, Plant Mol. Biol., 38:407-15 (1998).

Hirano et al., A single base change altered the regulation of the Waxy gene at the posttranscriptional level during the domestication of rice, Mol. Biol. Evol., 15:978-87 (1998).

Isshiki et al., A naturally occurring functional allele of the rice waxy locus has a GT to TT mutation at the 5' splice site of the first intron, Plant J., 15:133-8 (1998).

Kren et al., Gene repair using chimeric RNA/DNA oligonucleotides, Semin. Liver Dis., 19:93-104 (1999) [Abstract Only].

Kren et al., Targeted nucleotide exchange in the alkaline phosphatase gene of HuH-7 cells mediated by a chimeric RNA/DNA oligonucleotide, Hepatology, 25:1462-8 (1997).

Lamb et al., Cytochrome P450 immobilisation as a route to bioremediation/biocatalysis, FEBS Lett., 431:343-6 (1998).

McCouch et al., Molecular mapping of rice chromosomes, Theor. Appl. Genet., 76:815-29 (1988).

Pierrel et al., Catalytic properties of the plant cytochrome P450 CYP73 expressed in yeast. Substrate specificity of a cinnamate hydroxylase, Eur. J. Biochem., 224:835-44 (1994).

Sano et al., A trans-acting regulatory gene controlling the Wx gene expression and its temperature responses, Rice Genetics Newsletter, 2:17:121-7 (1985).

Tu et al., Transgenic rice variety 'IR72' with Xa21 is resistant to bacterial blight, Theor. Appl. Genetics, 97:31-6 (1998).

Vidal et al., High-efficiency biolistic co-transformation and regeneration of 'Chardonnay' (Vitis vinifera L.) containing npt-II and antimicrobial peptide genes, Plant Cell Rep., 22:252-60 (2003).

Wang et al., The amylose content in rice endosperm is related to the post-transcriptional regulation of the waxy gene, Plant J., 7:613-22 (1995).

Yoon et al., Targeted gene correction of episomal DNA in mammalian cells mediated by a chimeric RNA.DNA oligonucleotide, Proc. Natl. Acad. Sci. USA, 93:2071-6 (1996).

Zhang Jiwen et al., Screening and preliminary study on the chemical lethal mutant in rice photoperiod temperature sensitive male sterile line, Chinese J. Rice Sci., 13 (2): 65-68 (1999).

Zhang Jiwen et al., Weed Science, 21:2-5 (2001). [Chinese only.].

Cheng et al., Analysis of influence of Wx Intron 1 on gene expression in transgenic rice plant, Acta Phytophysiological Sinica, 27(5):381-6 (2001).

Haack et al., Eighth IUPAC International Congress of Pesticide Chemistry, Jul. 4-9, 1994 Sheraton Washington Hotel, Washington, D.C.Books of Abstract.

Mori, Inheritance of susceptible mutant in rice plant to herbicide bentazon, Japan. J. Breed., 34(Suppl. 1 ):421-2 (1984).

\* cited by examiner

```
cyp81A6-1       ...GTT CGG GAT GGG -AG GCG GAG GTG C...
                ...CAA GCC CTA CCC -TC CGC CTC CAC G...

TGCGCG caa gcc cua cCC CTC cgc cuc cac gT
       T
       T
RCO1
       T
     T
              3' 5'
```

Figure 9

```
Waxyᵃ           ...AAC ATC TGC AAG GTA TAC ATA TAT G...
                ...TTG TAG ACG TTC CAT ATG TAT ATA C...

TGCGCG uug uag acg uTC AAT uag uau aua cT
RCO2  T
      T
      T
      T
        TCGCGC AAC ATC TGC AAG TTA TAC ATA TAT GT
               3' 5'
```

Figure 10

CYP81A5    ... CT CGC GGC GCG CCG TGG TGG TGT CGT CGC CGG GGT GCG CCA GGG A...
           ... GA GCG CCG CGC GGC ACC ACC ACA GCA GCG GCC CCA CGC GGT CCC T...

CYP81A6    ... GT CGC GGC GCG CCG TGG TGG TGT CGT CGC CGG GGT GCG CCA GGG A...
           ... CA GCG CCG CGC GGC ACC ACC ACA GCA GCG GCC CCA CGC GGT CCC T...

CYP81A7    ...TGT CGT CGC CGG AGT GCG CCA GGG AGT GCT TCA CGG ACA ACG AT...
           ...ACA GCA GCG GCC TCA CGC GGT CCC TCA CGA AGT GCC TGT TGC TA...

CYP81A8    ...TGT CGT CGC CGG AGT GCG CCA GGG AGT GCT TCA CGG ACA ACG AC...
           ...ACA GCA GCG GCC TCA CGC GGT CCC TCA CGA AGT GCC TGT TGC TG...

TGCGCG aca gca gcg gCC -CT cgc ggu ccc uT

RCO3       T                         T
           T                         T
                       TCGCGC TGT CGT CGC CGG -GT GCG CCA GGG AT
                          3' 5'

Figure 11

```
CYP81A8        ...GAG ACG GAG GTG TCC CGG GGA GAT G...
               ...CTC TGC CTC CAC AGG GCC CCT CTA C...

TGCGCG ctc ugc cuc cAC TGG gcc cct cua Ct

RCO4        T                                      T
            T                                      T
            TCGCGC GAG ACG GAG GTG ACC CGG GGA GAT GT
                3' 5'
```

Figure 12

```
cyp81A6-2      ...CGC GTC CCC CGC -GG CGC CGC GCG C...
               ...GCG CAG GGG GCG -CC GCG GCG CGC G...
            TGCGCG gcg cag ggg gCG GCC gcg gcg cgc Gt RCO5        T                                      T
            T                                      T
            TCGCGC CGC GTC CCC CGC CGG CGC CGC GCG CT
                3' 5'
```

Figure 13

```
B1147A04       ...CGT GCC TCG GGA AGG AGA TGG CGT AT...
               ...GCA CGG AGC CCT TCC TCT ACC GCA TA...
            TGCGCG gca cgg agc gGT -CC tcu acc gca Ut
RCO6        T                                      T
            T                                      T
            TCGCGC CGT GCC TCG GGA  -GG AGA TGG CGT AT
                3' 5'
```

RICE BENTAZON AND SULFONYLUREA HERBICIDE RESISTANT GENE CYP81A6

CROSS-REFERENCE TO RELATED APPLICATIONS

This is the U.S. national phase application of International Application No. PCT/CN2005/000936, filed Jun. 28, 2005.

TECHNICAL FIELD

The present invention belongs to the technical field of genetic engineering, more particularly, it relates to mapping, isolation, and cloning of a novel rice gene that is resistant to bentazon and sulfonylurea, the two different kinds of herbicides used in paddy field. In addition, the present invention also provides uses of this new gene that is resistant to bentazon and sulfonylurea in improving some important agronomical character of various crops including rice, preventing selfing mixtures during the hybrid seed production. The present invention also relates to conduction of other locus/site-directed genetic manipulation based on use of the herbicide resistant gene of present invention.

TECHNICAL BACKGROUND

By utilization of heterosis of rice, China succeeded in developing of hybrid rice and this made the rice production increased substantially in total. Currently, China is large scaly exploring two-line system hybrid rice after success in utilization of the three-line heterosis based on nucleo-cytoplasmic interaction male sterility. The hybrid seeds of the two-line system are produced by photo- and thermo-sensitive genic male sterile line. But the sterility of this male sterile line is easily affected by environmental temperature, especially the midsummer low temperature that may cause its fertility restored. This thus results in a potential risk: when seed production of two-line system meets low temperature, the harvest seeds may comprise of false hybrid seeds (selfing seeds from male sterile line) mixed in the real hybrid seeds. Once presence of this mixture of the hybrid seeds with selfings from female parent and fail to eliminate them, it will causes a great loss to seed or field production. Guangxi in 1989 and Hunan in 1999 suffered such big loss right because of these.

The existing data proved that the seed purity declined 1 percent and yield of hybrid rice would reduce 75 kg per hectare. This is why the seed standard published by Chinese Ministry of Agriculture stipulates that the purity of hybrid seeds has to stand over 98%. Not only the photo- and thermo-sensitive male sterile line produced the two-line hybrid seeds have the selfing contamination problems, but so do the hybrid seeds when produced by incomplete male sterile lines, such as their sterility governed by nucleic major gene/s that have modifier gene/s participated in, or resulted from artificial chemical emasculation, or from environment sensitive nucleo-cytoplasmic interaction, or from artificially developed aneuploid. Many attempts have been made to eliminate such selfing mixture problems and thus to have the crop heterosis utilization establish on a more reliable foundation. However, in view of the characteristic of herbicide tolerant/resistant being widely used in the modern crop breeding program, not a few of scientists also attempt to utilize the wild-type rice that have the resistance to both bentazon and sulfonylurea to solve the above mentioned selfing mixture problems during the hybrid seed production.

There are two main categories of selective herbicides applied to rice. The former one is a benzothiadiazinone contact herbicide, such as bentazon, and its effective component can be absorbed through roots and leaves of crop. It kills the overwhelming dicot plants and sedges in most gramineous species excluding leguminous while it is harmless to rice. The herbicide mechanism of this herbicide is to inhibit Hill reaction in Photosynthesis. But the endogenous gene that is resistant to such herbicide of bentazon has not yet been cloned from plants so far. The later one is sulfonylurea-like herbicides explored by DuPont Company, which represent a new category of super effective herbicides characterized in high selectivity, broad spectrum, low poisons, and interior absorption. Among which, the tribenuron-ethyl, and bensulfuron-methyl and their complex formula are the most widely used herbicides in paddy field in China at present. The most notable characteristic of the sulfonylurea herbicides is the high activity, which makes their on-use dosage usually within 5-100 gram per hectare. The sulfonylurea-like herbicides are the acetolactate synthase (ALS) inhibitors, which have special effect to many annul or perennial weeds, especially the broadleaf weeds and are already widely used to eliminate the weeds growing in the field of rice, wheat, soybean, corn, canola, and lawn and other non-cultivated land. The DuPont Company has explored several sulfonylurea-resistant genes. One of these genes is SURB-Hra cloned from a tobacco ALS mutant. The SURB-Hra expresses resistance is because the mutated ALS is insensitive to the sulfonylurea. This gene has been applied to various crops including cotton and soybean (U.S. Pat. Nos. 5,013,659, 5,084,086, 5,141,870, 5,378,824, 5,605,011); Another sulfonylurea resistant gene developed by DuPont Company is the P450 su1 gene isolated from soil bacteria. The mode of action of this gene is to accelerate the metabolism of sulfonylurea to non-toxic. DuPont has made great efforts on the studies of this P450 gene and its application (see patent U.S. Pat. No. 5,349,127 for relevant information). In a patent (WO9708327) document, Japanese Nissan Chemical Corporation also publicized an ALS gene that was isolated from the cDNA of Kochia coparia, a kind of dicotyledonous broadleaf plant, having the function to make the transgenic plant resistant to sulfonylurea.

At present, two major approaches are applied to develop herbicide tolerant or resistant crops: the first one is by use of traditional physical/chemical mutagenesis to obtain the crop mutant capable to resistant or tolerant to herbicides; the second one is through recombinant DNA technology to introduce herbicide tolerant or resistant gene/s into the existing species to create the new materials tolerant or resistant to herbicides. Among which, the latter approach is the most widely used method. Currently, to enhance the crop herbicide tolerance or resistant, there are also two strategies involving in use of this recombinant DNA technology: first is to modify the herbicide target protein and make it insensitive to herbicide or over expressed to let plant still capable to normally metabolize the herbicide after absorption; second is to introduce in an new enzyme or enzyme system, such as P450 monooxygenase (Wang Guanlin and Fang Hongjun, 1998), to degrade or detoxify the absorbed herbicide before it functions.

Wild-type rice is naturally resistant to bentazon and sulfonylurea herbicides. Mori, a Japanese scholar and Zhang Jiwen et al from Hubei Academy of Agricultural Sciences made two recessive bentazon-sensitive-lethal mutants Norin 8m (Mori, 1984) and 8077S (Zhang Jiwen and Wu Xiaozhi, 1999) using X-ray radiation to treat Norin 8 and W6154, respectively. Based on these, Zhang et al (2001) further developed a selfing seed removal technology system to ensure the hybrid seed purity by use of the recessive mutant locus to tag the thermo-sensitive male sterile line. Since such a germplasm source plays an important role in the seed purity security and ensuring system of the two-line hybrid rice, e.g. use of on-8077S mutant locus tagged two-line's male sterile line could largely reduces the risk of seed production of the two-line hybrid rice, it is thus highly recognized by rice breeders and seed enterprises. However, since this hybrid seed purity-ensuring system functions only after seed-harvesting, even though its effect is not bad, it is hardly approved by seed administration department because what the technology ensured is the non-purified seeds and these are not according with the government-published seed purity standard before sale. Therefore, there is a need for creating a new mechanism to remove mixtures and to ensure the purity. However, the problem is that the gene controlling this trait has not yet been cloned for many years. It thus makes people have no way to conduct manipulation and further utilization of this trait, which has already become a major technical obstacle in this field.

Based on above situations, the present inventor used two existing bentazon sensitive lethal mutants as materials to conduct fine mapping of their mutant loci and finally cloned their common wild-type alleles through deepgoing investigation. Further on the base of this, the inventors developed several useful methods and techniques. These include a method for development of chemically supplemented emasculation and thermo-sensitive male sterile line, a genetic manipulation technique of double- or multi-sites targeted co-modification, a new approach for investigating biological function of plant genes, and a new technology for genetic improvement of plant traits. Therefore, this invention not only solves the selfing mixture problems during the hybrid seed production, but also provides the useful means with broad application perspective for investigating biological functions of genes and improving the biological traits genetically.

DETAILED DESCRIPTION OF THE INVENTION

An object of the present invention is to provide an already-isolated rice endogenous gene Cyp81A6, which is resistant to both bentazon and sulfonylurea herbicides (hereinafter referred to as Cyp81A6), and its functionally conservative variants, biologically active sub-fragments or derivatives with equal functions.

Another object of the present invention is to provide the cDNA sequence of the bentazon and sulfonylurea herbicide resistant gene, and its functionally conservative variants, biologically active sub-fragments or derivatives with equal functions.

Yet another object of the present invention is to provide a gene which is bentazon and sulfonylurea herbicide sensitive.

A further object of the present invention is to provide a recombinant vector which comprises Cyp81A6, its bentazon and sulfonylurea herbicide sensitive allele, or something with equal functions to both.

A still further object of the present invention is to provide polypeptides encoded by Cyp81A6, bentazon and sulfonylurea herbicide sensitive allele or something with equal functions to both.

Another object of the present invention is to provide genetically engineered cells that comprise Cyp81A6, bentazon and sulfonylurea herbicide sensitive allele or something with equal functions to both, or comprise the polypeptide encoded by Cyp81A6, or something with equal functions to both.

Yet a further object of the present invention is to provide a method which prevents the selfing mixtures during hybrid seed production.

Still another object of the present invention is to provide a new method for genetic manipulation directionally.

One more object of the present invention is to provide a new method for improving plant traits.

These and other objects and features of the invention will become more fully apparent when the following detailed descriptions are read in conjunction with the accompany drawings.

First of all, the present inventor conducted fine mapping of the bentazon and sulfonylurea herbicide sensitive lethal mutant loci identified in both 8077S and Norin 8m, and then isolated its resistant allele Cyp81A6 and the DNA fragment of promoter that regulate this gene from wild-type indica rice. This gene can be utilized to improve the characteristic of the resistance to bentazon and sulfonylurea herbicides for most of the soybean-excluded dicotylandon and cyperaceae weed plants.

The bentazon and sulfonylurea herbicide resistant gene provided by the present invention comprises a kind of nucleotide sequence selected from the following groups consist of:
(1) a nucleotide sequence having the nucleotide sequence shown in SEQ ID NO.1;
(2) The nucleotide fragments or derivatives thereof, which have the equal functions as the nucleotide sequences of position 1949 through 4216 of SEQ ID NO.1;
(3) a nucleotide sequence having the nucleotide sequence shown in SEQ ID NO.2;
(4) The nucleotide fragments or derivatives thereof, which have the equal functions as the nucleotide sequences of position 54 through 1595 of SEQ ID NO.2;
(5) a nucleotide sequence that can hybridize with the nucleotide sequence shown in SEQ ID NO.1 or SEQ ID NO.2 under the stringent conditions.

Preferably, the said isolated rice endogenous bentazon and sulfonylurea herbicide resistant gene comprises the nucleotide sequence as shown in SEQ ID NO.1; the cDNA of the said isolated rice endogenous bentazon and sulfonylurea herbicide resistant gene comprises the nucleotide sequence as shown in SEQ ID NO.2.

The present invention provided polypeptides encoded by the rice endogenous bentazon and sulfonylurea herbicide resistant gene comprise the polypeptide of the amino acid sequence encoded by one of the nucleotide sequences selected from the following groups consist of:
(1) a nucleotide sequence having the nucleotide sequence shown in SEQ ID NO.1;
(2) a nucleotide fragments or derivatives thereof, which have the equal functions as the nucleotide sequences of position 1949 through 4216 of SEQ ID NO.1;
(3) a nucleotide sequence having the nucleotide sequence shown in SEQ ID NO.2;
(4) a nucleotide fragments or derivatives thereof, which have the equal functions as the nucleotide sequence of position 54 through 1595 of SEQ ID NO.2;
(5) a nucleotide sequence which can hybridize with the nucleotide sequence as shown in SEQ ID NO.1 or SEQ ID NO.2 under the stringent conditions;

The amino acid sequence comprises the amino acid sequence shown in SEQ ID NO.3 is preferred;

The present invention also provides a genetic manipulation method of co-modification of the target sequences simultaneously at double or multiple sites of genome in the living cells. The characteristics of this method take the nucleotide sequence that can be used as selectable marker after modification as the first modification target and take the key base of the target gene of living cells as additional modification target. Use co-introduction technology to introduce double or multiple RNA•DNA chimeric oligonucleotides-RCOs designated for targeted modification of different target nucleotide sequences into the recipient cells, so that they can simultaneously modify or mutate both target sites as mentioned above. Then, further utilizes the modified phenotype of the above mentioned nucleotide sequence that can be used as selectable marker after modification to conduct indirect selection of genotype resulted from endogenous gene target after targeted modification or mutation.

In the above genetic manipulation methods, the nucleotide sequence which can be used as selectable marker after targeted modification includes but not limits to the mutated or non-mutated herbicide resistant/sensitive gene, antibiotics resistant gene, biological or chemiluminescence gene, enzyme gene etc. The technicians in this field may select them freely according to general knowledge. Among which, the herbicide resistant/sensitive gene is the prior choice, especially those possess the nucleotide sequence as shown in SEQ ID NO.1 or SEQ ID NO.2 or its sub-fragments or derivatives which have the same function, or those have a deletion of the 2455th base C or the 4006th base G in the nucleotide sequence shown in SEQ ID NO.1, or those has a deletion of the 560th base C or the 1385th base G in the nucleotide sequence shown in SEQ ID NO.2.

Present research indicated that the isolated-bentazon and sulfonylurea herbicide resistant gene encodes a cytochrome P450 protein, which has been formerly designated as CYP81A6 according to the international standard classification and nomenclature system. This protein contains the conservative motifs present in common P450 proteins and its amino acid sequence is listed in SEQ ID NO. 3. At present, although the several herbicide resistant P450 genes has been cloned from plants, such as the CYP71A11 and CYP81B2 (by Yamada etc, 2000) in tobacco, CYP71A10 (by Siminszky etc, 1999) in soybean, CYP73A1 (by Pierrel etc, 1994) and CYP76B1 (by Didierjean etc, 2002) in Chinese sorghum, as well as the CYP71B1 (by Lamb etc, 1998) in hlaspi arvensae. But the similarities between these P450 genes and CYP81A6 gene are all less than 40%, and they all cannot degrade the bentazon and sulfonylurea herbicides. These results reveal that the CYP81A6 gene is a novel category of herbicide resistant gene. Therefore, this invention refers to use of this novel herbicide resistant gene that is operatedly linked either to itself promoter or to other constitutive or tissue specific promoter and development of novel herbicide resistant plant lines by introduction of it into the bentazon and sulfonylurea sensitive species, those of broadleaf plants except leguminous or cyperaceae weeds.

As shown in the present invention, the expression of DNA fragment is in a constitutive manner. Therefore, be able to utilize the antisense RNA or RNAi of this gene in connecting with the anther specific promoter, such as Osg6B and RA39 etc, then by introduction of it into the thermo-sensitive male sterile lines of the rice (not limited to rice) to let this gene unable to express in the anthers, so that able to use the sulfonylurea herbicide to kill the pollens and create a new chemically supplemented emasculation and thermo-sensitive male sterile line.

Besides, the present invention identified two bentazon and sulfonylurea herbicide sensitive Cyp81A6 single-base deletion mutant sites provide modifiable targets for gene-targeted mutation. Therefore, be able to utilize the artificially designated RCOs molecules for targeted repair of Cyp81A6 mutant sites to recovery their resistant to bentazon and sulfonylurea herbicides and thus to meet with the selection purpose. With the aid of these two mutant genes, be able to design and introduce two or more kinds of RCO molecules aiming at different targets simultaneously. Among which, one molecule is used to directionally repair the single-base deletion site of Cyp81A6 gene and for resuming its resistance to bentazon and sulfonylurea herbicides for creating selectable marker; and another one or more are used to directionally mutate the target endogenous genes and then according to the phenotype or biochemitype differences presented between the mutants and wild controls deduce their exact biological functions or conduct pure line selection based on the mutated target genes to obtain the desired new varieties or lines with improved agronomic traits. Besides, it is also able to indirectly select the genotypes of the target genes based on the selectable modification phenotype of other gene locus or a co-introduced foreign selectable marker gene.

In addition, there is possibility for make use of the above technology or other DNA homologous recombination technology or physical or chemical mutagenesis technology to mutate the Cyp81A6 gene either directionally or randomly and thus to change its functions and create a new bentazon and sulfonylurea herbicide sensitive lethal mutant, which is capably used for selfing seed-removing and hybrid seed purity-ensuring. Besides, the cloned wild-type allele can endow most of the broadleaf plants except leguminosae or cyperaceae weeds with the character of bentazon and sulfonylurea herbicide resistance after genetic transformation.

The Cyp81A6 coding sequence is widely preserved in plants of different species. Therefore, the primer and the probe at a length about 8 nucleotides or more copied from the rice Cyp81A6 and its derivative sequence can be used for isolation and cloning of the homologous genes of other species in gramineae family. Use of the above method is able to clone the gene that has high similarities with rice Cyp81A6. Fuse this gene sequence to the appropriate plasmid vector and then introduce it into the genome of the plant sensitive to bentazon and sulfonylurea herbicides, so that be capable to generate transgenic lines with the resulted bentazon and sulfonylurea herbicide resistant.

The meanings of following terms used in this description and Claim are familiar to and frequently used by the skilled in the art. Demonstrative brief description to some terms is as follows.

The term "Nucleotide sequence" used herein refers to single-nucleotide, nucleotide and multi-nucleotide and their segments or parts, or even genome or synthesized DNA or RNA. They can be either single-chain or double-chain, representing the sense chain or antisense chain.

"Sub-fragments with equal functions", "biological active sub-segments with equal functions" refer to a part or sub-sequence of the isolated DNA fragments, hereinto, no matter whether these segments or sub-sequences encode functionally active proteins, they preserve the ability to change gene's expression pattern or generate certain herbicide resistance. For example, the above-mentioned fragments can be used for the designation of chimeric gene or antisense inhibition of native gene. "Derivatives with equal functions", "functionally conservative mutants" mean the entire, or more, or partial sequences of the isolated DNA fragments. Among which, no matter whether these fragments encode active protein, they all preserve the ability to change gene's expression pattern or generate certain herbicide resistance, and can be used for designing of chimeric gene or antisense inhibition of native gene.

"Mutant" used herein refers to a kind of amino acid sequences or polynucleotide sequences that possess one or few amino acid residue or nucleic acid base changes. The mentioned changes include the deletion, insertion or substitution etc of amino acid residue/s or nucleotide base(s in the amino acid sequence or nucleotide sequence. The "mutant" mentioned in this invention possesses conservative change, in which the changed amino acid sequence has the structural or chemical property similar to the original amino acid sequence. The mutant of such polynucleotide can be generated either naturally or artificially. These nucleotide mutants include substitution, deletion and insertion etc. As known in this field, the allelic variant is a replacement form of polynucleotide, it can be the substitution, deletion and insertion of one or more nucleotides, but does not essentially change the functions of its encoded polypeptide.

The term "amino acid sequence" as used herein, refers to an oligopeptide, polypeptide, peptide or protein sequence, or a fragment of any of these. The polypeptide or protein as used herein, are not meant to limit them to the complete native amino acid sequence associated with the recited polypeptide or protein molecule.

"Homology" can be determined electronically, e.g., by using the MEGALIGN program (Lasergene software package, DNASTAR.Inc. Madison Wis.). TheMEGALIGN program can create alignments between two or more sequences according to different methods, e.g., the cluster method. (Higgins, D. G. and P. M. Sharp (1988) Gene 73: 237-244). Percent identity between nucleic acid sequences can also be calculated by the cluster method, or by other methods known in the art, such as the Jotun Hein method. (See, e.g., Hein, J. (1990) Methods in Enzymology 183: 626-645.)

The term "Stringent conditions" used herein refers to: (1) Molecular hybridization and strip/wash off under lower ionic strength and higher temperature. such as strip off under 0.2× SSC, 0.1% SDS, 60° C., or (2) Add denaturant upon hybridization, such as 50% (v/v) formamide, 0.1% bovine serum/ 0.1% Ficoll, 42° C. etc; or (3) The identity between two sequences is at least 95% but the hybridization will take place only when the identity is over 97%. And, the polypeptide-encoding polynucleotide capable for hybridization has the same biological functions as the polypeptide-encoding nucleotide shown in SEQ ID NO.1.

"Vector" used in the present invention refers to the bacterial plasmids, bacteriophage, yeast plasmid, or plant cells' virus, etc. The applicable vectors in this invention include *Agrobacterium tumefaciens vector, E. coli* plasmid vector and virus vector etc. Anyway, as long as it is capable to replicon and stably inherited in the body of host, any plasmid and vector can be used to construct the recombined expression vector of this invention.

"Cells of host" used herein refers to the genetic engineering host cells into which the nucleotide sequence of this invention may be introduced or that contain the recombinant vectors of the nucleotide sequence of this invention. These cells include the mustard, solanaceae, cyperaceae, convolvulaceae, malvaceae, and linaceae plant cells etc.

The "sulfonylurea herbicide" is a category of herbicides with super-high efficiency, broad spectrum, low poison and high selectivity. Its biological activity is 100-1000 times higher than those of the traditional herbicides. It can be absorbed by the plant's root, stem and leaf. It acts on acetolactate synthase and inhibits the biosynthesis of branched-chain amino acids leucine, isoleucine and valine, thus leading to preventing biosynthesis of proteins that are required by plant. Consequently, the growth of the sensitive plant is stopped. What the Cyp81A6 gene in this invention resists includes but not limit to the sulfonylurea herbicides listed in Table 1.

TABLE I

Main sulfonylurea herbicides for paddy-field weed prevention

| General name | Developed by | Dosage(g/ha) |
|---|---|---|
| Metsulfuron-methyl | DuPont | 3.0-7.5 |
| Tribenuron-ethyl | DuPont | 9.0-18.0 |
| Bensulfuron-methyl | DuPont | 20.0-30.0 |
| Pyrazosulfuron-methyl | Japanese Nissan Chemical Corporation. | 20.0-50.0 |

In addition, the nucleic acid sequence of this invention or the transforming host cells that contain the recombinant vector of nucleic acid sequence of this invention can be processed by the routine techniques that the technicians in this field are familiar with. When the host is prokaryotic organism, such as *E. coli*, the CaCl2 method, electroporation method etc can be applied. When the host is eukaryotic cell/s, *Agrobacterium tumefacien*, biolistic, direct DNA transformation method, calcium phosphate coprecipitation method, microinjection method or liposome package etc can be selected to use.

BRIEF DESCRIPTION OF THE DRAWINGS

FIG. 9. The target sequence of Waxa gene and the RNA-DNA Chimeric Oligonucleotide RCO1, which is designed accordingly.

FIG. 10. The target sequence of cyp81A6-1 gene and the RNA•DNA Chimeric Oligonucleotide RCO2, which is designed accordingly.

FIG. 11. The target sequences of Cyp81A5, Cyp81A6, Cyp81A7, Cyp81A8 genes and the RNA•DNA Chimeric Oligonucleotide RCO3, which is designed accordingly.

FIG. 12. The target sequence of Cyp81A8 gene and the RNA•DNA Chimeric Oligonucleotide RCO4, which is designed accordingly.

FIG. 13. The target sequence of cyp81A6-2 gene and the RNA•DNA Chimeric Oligonucleotide RCO5, which is designed accordingly.

FIG. 14. The target sequence of rice P450 gene (the GenBank accession number is B1147A04) whose functions are unidentified and the RNA•DNA Chimeric Oligonucleotides RCO6, which is designed accordingly.

Figure 1:
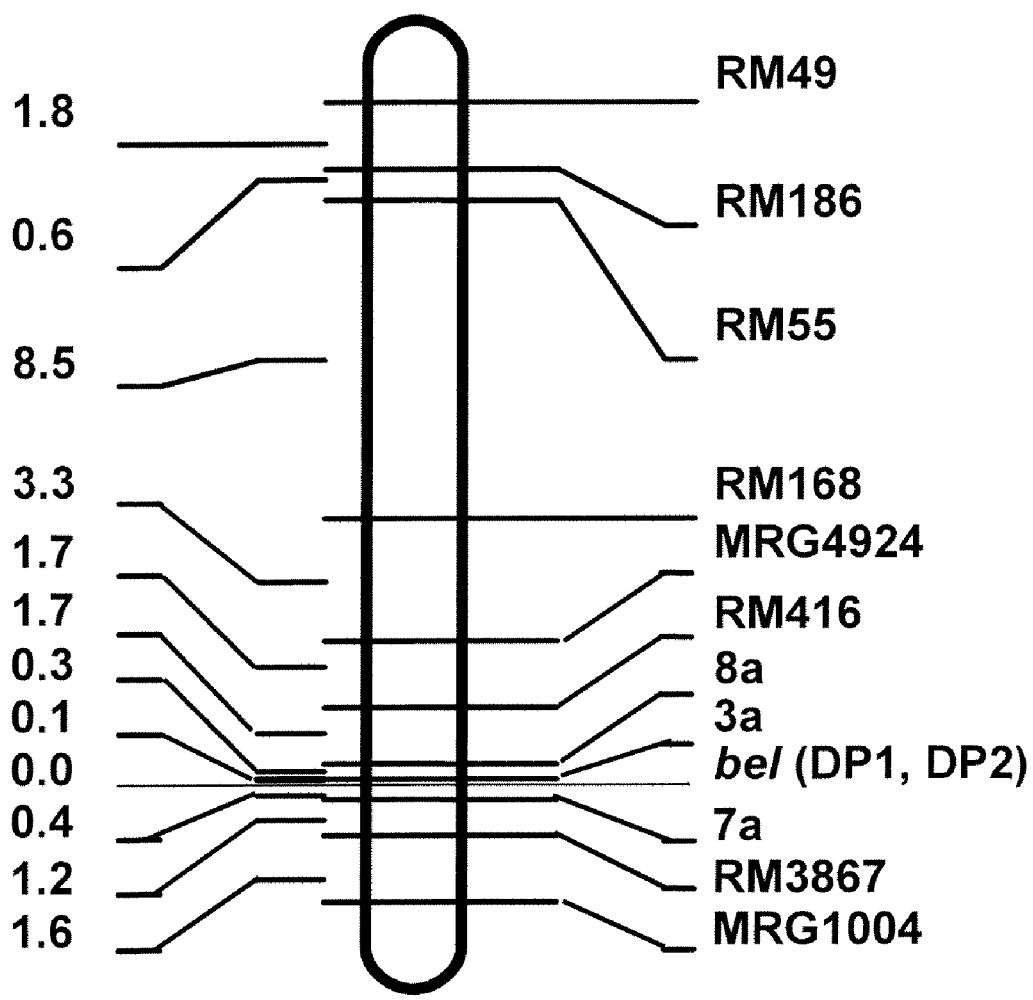
FIG. 1. The position of rice bentazon sensitive lethal mutant site bel of this invention and its co-separated PCR-RFLP markers DP1 and DP2 on molecule marker genetic linkage map of the chromosome 3.

SEQ ID NO.1: comprising Cyp81A6 coding sequence and Cyp81A6 promoter.

SEQ ID NO.2: the full length cDNA sequence of Cyp81A6 gene.

SEQ ID NO.3: the amino acid sequence encoded by Cyp81A6 gene.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. Generally, the implementation examples without indications of the experimental conditions and testing methods shall be operated under general conditions such as those mentioned in Molecular Cloning: A Laboratory Manual, (Third edition by Sambrook, 2001 Cold Spring Harbor Laboratory Press,) or according to the manufactory instructions known in the prior art.

EXAMPLES

Example 1

Fine Mapping and Cloning of Target Gene

1. Fine Mapping of Bentazon Sensitive Lethal Gene Bel in Indica Mutant 8077S 1.1 Mapping Population The mapping population used in this Example was consisted of F2 recessive individual plants. While constructing, firstly, make use of Peiai 64 backcrossing line that carries the recessive bel locus (hereinafter referred to as Peiai 64S) to cross with 93-11, a wild-type thermo-sensitive male sterile restorer line (bred by Agricultural Science Research Institute of Li-Xia-He District, Jiangsu Province) for obtaining F1. Then, reproduce F2 offspring selfing from F1 generation, with the population up to 1,000 plants in total. When the seedlings grow to 3-4 leaves after sowing, treat all F2 plants by cutting leaves one by one (cut about 1 cm from the leaf apex) and smearing with bentazon (the 25% bentazon aqueous produced by Jiangsu Sword Agrochemicals Co., Ltd.) at a concentration of 1250 mg/L, three leaves per plant. Then, select 231 individual plants homozygous for recessive bel locus as the mapping population of this example based on the sensitivity of treated leaves to bentazon.

1.2 DNA Extraction

Total DNA was extracted from fresh leaves collected from both parental plants of 93-11 and Peiai 64m as well as F2 offspring of 231 bentazon-sensitive lethal homozygates, respectively, using CTAB method as described previously by McCouch etc (1988). The chemicals used for this purpose were all purchased from Shanghai Sangon Biological Engineering Technology And Service Co., Ltd. (hereinafter referred as Shanghai Sangon).

1.3 SSR Analysis and Fine Mapping of Bel Gene

The SSR amplification reaction system is: 50 ng template DNA, 1×PCR reaction buffer solution, 1.87 mM Mg2+, 0.2 mM dNTP, 1.0 u rTaq enzyme [TaKaRa Biotechnology (Dalian) Co., Ltd., namely Takara Biotech, hereinafter referred to as "Takara"], and forward and reverse primers, 0.2 µM for each. The total volume of reaction per tube is 20 µl. The amplification was programmed as follow: initial denaturation step at 95° C. for 3 min was followed by 35 cycles of 94° C. for 1 min, 60° C. for 1 min and 72° C. for 1 min with a final extension at 72° C. for 5 min and then stored forever at 10° C. The resulted PCR products were separated with 3.5% agarose gel (from Shanghai Sangon). After that, the gels were stained with EB (from Shanghai Sangon) and pictures were taken by UVP imaging system (Germany).

In the previous work, the inventors had primarily mapped the bel locus existing in 8077S onto the long arm of rice chromosome 3 using SSR markers, with the defined genetic distance about 7.1 cM from one of them, namely RM168 (Zhang et al 2002). In order to further fine map this locus, the present inventors redesigned and synthesized a set of new SSR markers located between RM168 and the end of long arm of chromosome 3 based on genomic sequence analysis with the aid of SSR primer search software SSRHunter 1.3. These SSR markers include 7a (forward primer: 5'-GTCAGAGCAAGGTCGGAGAG-3' (SEQ ID NO: 4); reverse primer: 5'-TCGGTGATCATTGTCATTTG-3') (SEQ ID NO: 5), 3a (forward primer: 5'-TGTTTTCTTTTTCGCTGTGTG-3' (SEQ ID NO: 6); reverse primer: 5'-GCAAGCCTTTTTGCGTATTC-3') (SEQ ID NO: 7) and 8a (forward primer: 5'-GCTTCCCTCTCCTTCCACTT-3' (SEQ ID NO: 8); reverse primer: 5'-CTTGTGAGTGAGTGGTGACG-3') (SEQ ID NO: 9), etc (The primer sequences were all synthesized by Shanghai Sangon). Among which, the 3a and 7a are located on the same BAC clone AC084282. Use of 8a marker, four out of 231 the extreme individual plants with pure recessive locus were detected as recombinants from single-exchange, and other four of such individual plants were detected for 7a marker. These results further verified that the bel was located between these two SSR markers. In addition, only one single-exchange recombinant plant was detected by use of 3a marker near to 8a, this thus indicating that the bel was located in a shorter region from 3a to 7a. The fine map (FIG. 1) of bel locus is constructed using MAPMARKER3.0. The genetic distance from marks 3a and 7a to the bel locus were calculated no longer than 0.1 cM and 0.4 cM, respectively.

2. Deduction, Isolation, and Cloning of Candidate Genes 2.1 Deduction and Sequence Analysis of Candidate Genes The results of sequence analysis showed that there are totally 18 putative genes between the SSR markers 3a and 7a, which includes a cluster of four cytochrome P450 genes (the accession no in GenBank as AAK63940.1, AAK63920.1, AAK63922.1 and AAK63925.1 respectively), which are named formally as Cyp81A5, Cyp81A6, Cyp81A7 and Cyp81A8 according to the international standard classification and nomenclature system. The previous reports showed that the P450 gene in rice microsome was involved in detoxification of bentazon (Haack etc, 1994). Furthermore, Deng and Hatzios (2003) isolated and purified a P450 protein with a molecular weight of 60 kDa from the seedlings of rice and they confirmed that it plays an important role in degradation metabolism of herbicide BSM (bensulfuron-methyl). The data present above all implied that there was an association between the bel and P450 and we thus considered that cluster of four P450 genes as mentioned above as candidate genes.

To further define the candidate genes more precisely, we synthesized four sets of specific primers (Table 2) according to the genome sequence of four P450 genes, respectively. Each of the above deduced candidate genes was amplified from both wild control W6154S and mutant 8077s, respectively, using high fidelity Pyrobest™ polymerase (Takara), and then directly sequenced by Perkin Elmer AMI 377 (Shanghai GeneCore BioTechnologies Co., Ltd., hereinafter referred to as Shanghai GeneCore). The sequence analysis showed that no differences were observed in Cyp81A5, Cyp81A7, and Cyp81A8 except that a single base G deletion was appeared in Cyp81A6 derived from mutant 8077S as compared with the wild control W6154 (the 4006th base of the sequence shown in Sequence Table SEQ ID NO.1). We therefore took the Cyp81A6 as the sole candidate gene.

The primers used for PCR amplification and sequencing of the above mentioned four genes (the sequence is synthesized by Shanghai Sangon) were: Cyp81A5: P1-1a and P1-1b, P1-2a and P1-2b, P1-3a and P1-3b; Cyp81A6: P2-1a and P2-1b, P2-2a and P2-2b, P2-3a and P2-3b, P2-4a and P2-4-b, P2-5a and P2-5b, P2-6a and P2-6b; Cyp81A7: P3-1a and P3-1b, P3-2a and P3-2b, P3-3a and P3-3b; Cyp81A8: P4-1a and P4-1b, P4-2a and P4-2b, P4-3a and P4-3b. The sequence of each primer is listed in Table 2.

2.2 Allelism Test of the Bel Between Japonica and Indica Rice

Figure 2:
FIG. 2. Allelism test of bentazon sensitive lethal sites in Norin 8m and 8077S. a: the plants before bentazon treatment, left: Norin 8m; right: 8077S; middle: the F1 hybrid of Norin 8m and 8077S. b: the plants one week after the bentazon treatment. The applied concentration of bentazon is 1250 mg/l.

As mentioned above, the Japanese scholar Mori obtained a bentazon sensitive lethal mutant Norin 8m by γ-ray radiation treatment of Norin 8 (Mori, 1984). Classical genetic analysis indicated that this mutant was controlled by a pair of recessive alleles. In order to verify whether the bentazon sensitive loci in both 8077S and Norin 8m are allelic, we made a cross between 8077S and Norin 8m and obtained the F1 hybrid and its selfed F2 population containing 800 plants. After sowing, when the seedlings grew to 9-10 leaves, sprayed bentazon onto the surface of leaves of both the parents and their derived F1 plants at a concentration of 1250 mg/L. All the treated plants withered and died one week later (FIG. 2). These results primarily verified that the bentazon sensitive loci in the two mutants are allelic to each other. Moreover, all of the treated 800 F2 plants from sefled F1 plants were also withered and died too, thus further confirming the above results. To distinguish the loci originated from 8077S and that originated from Norin 8m, we named them as cyp81A6-1 and cyp81A6-2, respectively.

Together with high fidelity Pyrobest™ polymerase (Takara), oligonucleotide primers listed in Table 2, which specific to CYP81A6 have been used to amplify the wild allele Cyp81A6 and the mutant cyp81A6-2 from wild type Norin 8 and mutant Norin8m, respectively, and then the products were sequencing in Shanghai (Perkin Elmer AMI 377, Shanghai GeneCore). The results revealed that the cyp81A6-2 from the mutant Norin 8m had a single C deletion as compared with the wild allele of Cyp81A6. This single C deletion was at the 2455th base of the sequence as shown in SEQ ID NO.1. These data again verified the result of allelic test.

TABLE 2

Specific primers used in PCR amplification

| Primer name | Primer sequence (5'-3') | SEQ ID NO |
|---|---|---|
| P1-1a | GCTGTGCGTATCCAATGAAG | 10 |
| P1-1b | TCAGGGAGAGCTCGAACAG | 11 |
| P1-2a | CTCATGTCGGGGCTCATC | 12 |
| P1-2b | TAGCTTTCTCCCGATTGACC | 13 |
| P1-3a | TTCATGACCCAGACGAAAAA | 14 |
| P1-3b | ATGAGTTTGCCCTGGAGATG | 15 |
| P2-1a | TGAGAAGACCAAGGCAGGAG | 16 |
| P2-1b | GGCAACAAATCGACACACG | 17 |
| P2-2a | GGCTGCCTCCTCCTCTCT | 18 |
| P2-2b | TGAGGATCGAGAGTCCGAGA | 19 |
| P2-3a | AATAATCGCCCAACGATTGA | 20 |
| P2-3b | GGAGACAATCCAGGCATCTC | 21 |
| P2-4a | GATCGCATCTGCGTTTCAG | 22 |
| P2-4b | GATGAGCCCCGACATGAG | 23 |
| P2-5a | CCTCATGTCGGGGCTCAT | 24 |
| P2-5b | CGCACCAATGAGAGAATTCAG | 25 |
| P2-6a | AAATCTTAGTTCCACCCTCTTGC | 26 |
| P2-6b | TCGTCCTGGAGATGCAAAC | 27 |
| P3-1a | TGCGTAATACAACTTACTATTTCCGTA | 28 |
| P3-1b | GAACAGCCTCCGCTTCAG | 29 |
| P3-2a | ATGGTGCAGAGGATGTACCG | 30 |
| P3-2b | TTCAAATTAAGCGTTCAAAATTCA | 31 |
| P3-3a | ACCCCTTTTCCTCTTTCGTG | 32 |
| P3-3b | GATGAAGCCTACCTGGTGGA | 33 |
| P4-1a | CCTCAAGGCTCAAGCATCAT | 34 |
| P4-1b | GAACAGCCTCCGATTCAGC | 35 |
| P4-2a | ACATGGTGCGGAGGATGTA | 36 |
| P4-2b | TGGTTTCTGATCAAGCGTTTT | 37 |

TABLE 2-continued

Specific primers used in PCR amplification

| Primer name | Primer sequence (5'-3') | SEQ ID NO |
|---|---|---|
| P4-3a | AGGCATGTTTCGAATTGTACTT | 38 |
| P4-3b | AACTTTATTCCCTGCTACACAGC | 39 |

2.3 PCR-RFLP Analysis

Figure 3:
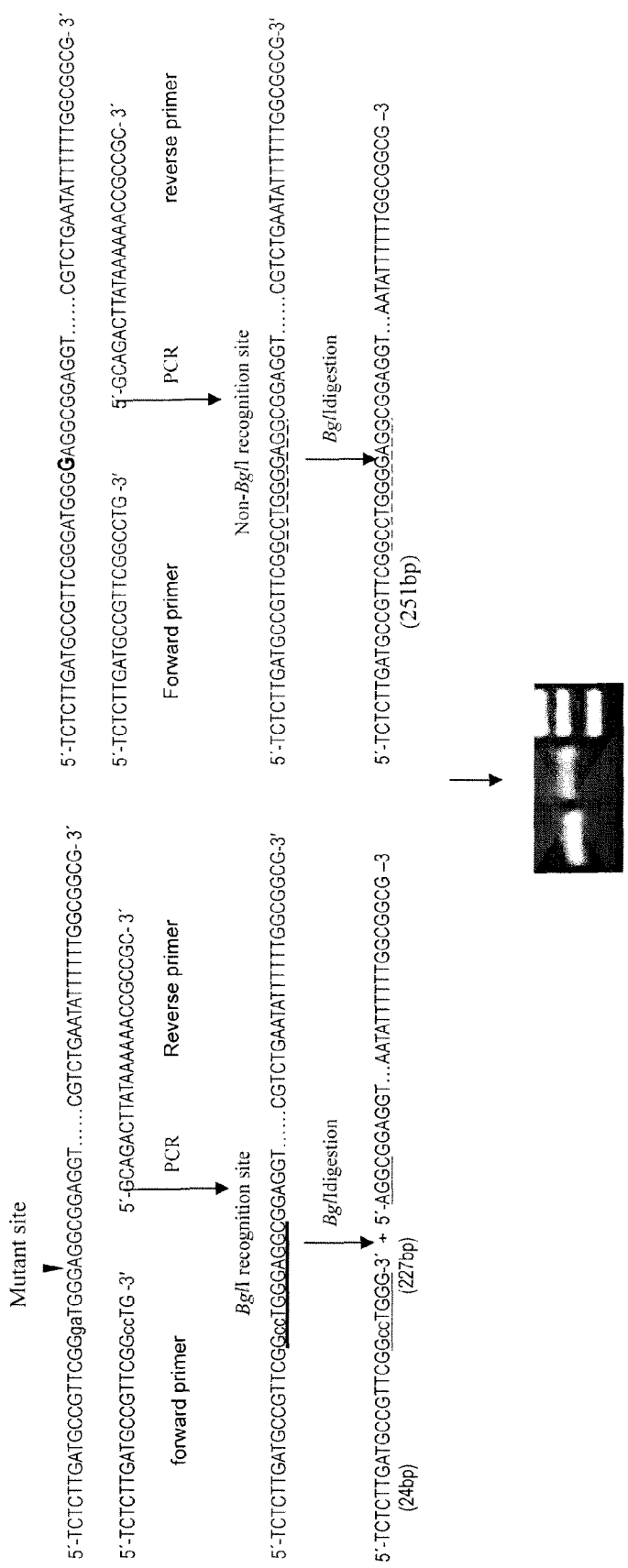
FIG. 3. Flow chart of PCR-RFLP analysis to verify the cyp81A6-1 single-base deletion site in 8077S. Note the marks in the figure for the mutation site, primer sequence for PCR specific amplification, the manually introduced BglI digestion site through primer designing, as well as the restriction length polymorphism between PCR products from the target sequences with or without manually introduced BglI digestion site.
Figure 4:
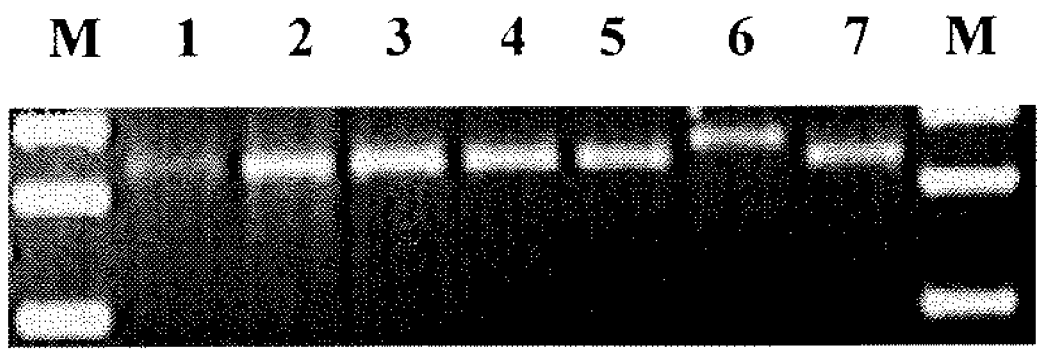
FIG. 4. PCR-RFLP analysis results of mapping population. M: 100 bp DNA Ladder (Takara); 1-5: five DNA mixture samples (46 plants/sample) from F2 mapping population (recessive sensitive lethal homozygous lines); 6: 93-11; 7: Peiai 64m.

To prevent the sequence errors that might be resulted from the sequencing analysis, we further tested and verified the single-base deletion of cyp81A6-1 and cyp81A6-2 in two mutants by PCR-RFLP analysis. During the experiment, we first compared and analyzed the wild and mutating sequence flanking the cyp81A6-1 single-base deletion site using WEB-CUTTER 2.0 software to check whether there was any restriction enzyme cutting sites that was changed or newly generated after mutation. To the mutant of cyp81A6-1 without such site, we directionally mutated bases G and A nearby the upstream of the deletion site to two C bases by substitution through primer designing to create a new artificial BglI cutting site (GCCNNNNNGGC). The further testing data showed that the amplified products containing this fragment of the modified sequences from wild control material could not be acted as recognition and digestion site by BglI since it had an extra base G as compared to the mutated allele. After digestion with BglI enzyme, only one belt at a length of 251 bp appeared on the gel; for the mutated allele, however, the PCR amplified products could result in two belts after digestion with the same enzyme. Among which, one belt had length of 24 bp and anther one had length of 227 bp (FIG. 3). Furthermore, applied the same PCR-RFLP primers to amplify DNA samples from 93-11 and Peiai 64m as well as five bulks of DNA mixtures (46 plants per bulk) derived from F2 mapping population. The obtained amplification products were then purified by PCR-specific purification kit (Takara) and subjected to BglI digestion and the resulted belt-types from all of the F2 DNA bulk samples were exactly the same as that of parental DNA sample extracted from Peiai 64m (FIG. 4). These results thus confirmed that the polymorphism BglI-PCR-RFLP marker artificially introduced to the cyp81A6-1 deletion site was indeed co-segregated with cyp81A6 gene. We therefore named this marker as DP1 (FIG. 1).

Figure 5:
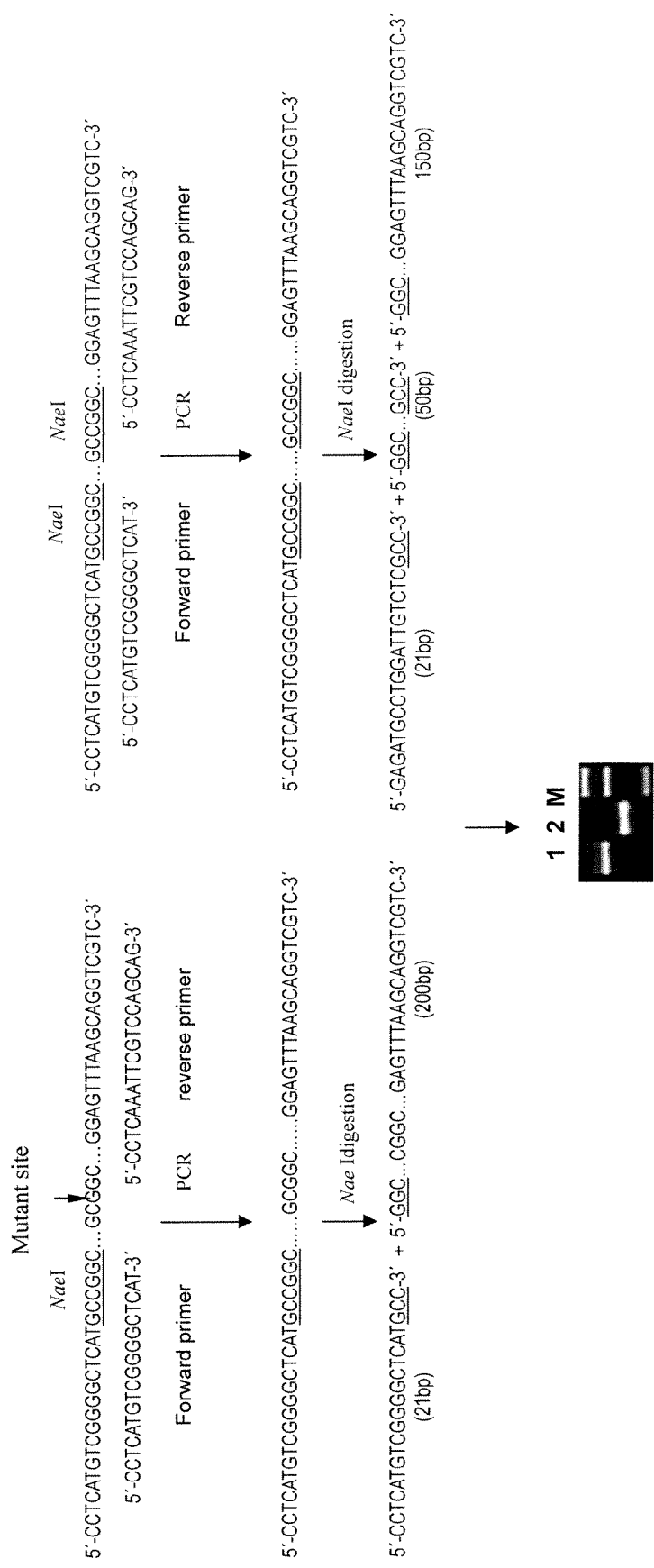
FIG. 5. Flow chart of PCR-RFLP analysis to verify the cyp81A6-2 single-base deletion site in Norin 8m. Note the marks in the figure for the mutation site, primer sequence for PCR special amplification, the original NaeI restriction site on wild-type Cyp81A6 sequence corresponding to cyp81A6-2 single-base deletion site, as well as the restriction length polymorphism between PCR products from the target sequences with or without manually introduced NaeI digestion site.

As for the cyp81A6-2 mutant, use the same WEBCUTTER 2.0 software to analyze restriction sites between its wild-type and mutant DNA sequences and the single-base deletion of C in the mutant site was found just occurred in NaeI (GCCGGC) enzyme recognition site, this thus no longer cut by the NaeI enzyme. However, another NaeI enzyme digestion site located at 50 bp of its upstream (within the PCR amplification scope) was still maintained. The further PCR-RFLP analysis (see also FIG. 5 for technical flow) indicated that the PCR amplification products obtained from wild Norin 8 and purified by Takara PCR-specific purification kit were cut into three belts (21 bp, 50 bp and 151 bp) by this NaeI (Takara) enzyme, whereas the PCR amplification products from mutant Norin8m subjected to the same purification procedure could not be cut by NaeI enzyme on the single base deletion site, thus producing only two belts with the sizes of 21 bp and 200 bp (FIG. 5). Similar to the PCR-RLP analysis made on cyp81A6-1, these results also confirmed that the polymorphism NaeI-PCR-RFLP marker originally existing in the cyp81A6-2 deletion site was really co-segregated with Cyp81A6 gene. We therefore named this marker as DP2 (FIG. 1). Moreover, these results further verified the sequencing results mentioned above.

Figure 6:
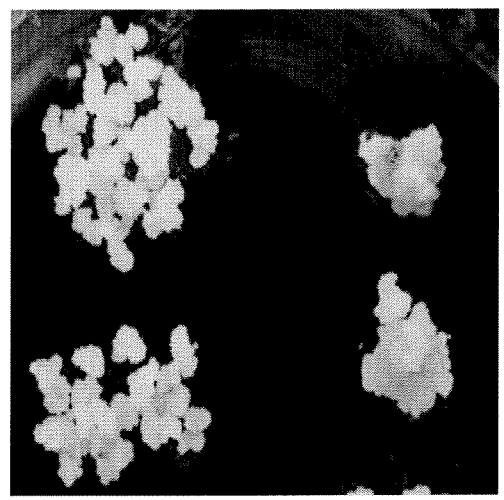
FIG. 6. Bensulfuron-methyl selection results of Cyp81A6-transformed 8077S calli. Left: transgenic; right: non-transgenic control.
Figure 7:
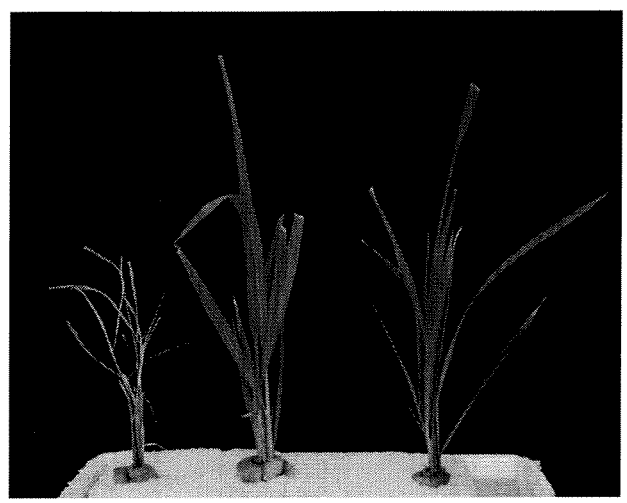
FIG. 7. Bentazon test results of Cyp81A6 transgenic 8077S seedlings. Left: negative control of 8077S; middle: transgenic seedling; right: positive control of W6154S.

2.4 Cloning of Candidate Gene Cyp81A6 and Complementary Confirmation of its Biological Functions The full length sequence of candidate gene Cyp81A6 was obtained through lump-sum amplification using LA TaqTM polymerase reagent kit purchased from Takara Company. The long fragment PCR specific primer pairs (forward primer: 5'-CAAACTTCCAACTTTCCCGTCACCTTCACT-3' (SEQ ID NO: 40); reverse primer: 5"-CCGCGGGTCAC-CGAGCAGAAAGCCCTTCCT CCCAAGTTAGAA-3' (SEQ ID NO: 41), synthesized by Shanghai Sangon) used in this experiment were designated at a start from 124 bp before and end with 4145 bp after BamHI enzyme digestion site located at 5'-end of Cyp81A6 gene, respectively, according to the DNA sequence publicized by indica rice genome database. According to the designing, these primers have a BstEII enzyme cutting site attached to the 3'-end of the primers, which is convenient for production of cohesive end and ligation during cloning. The amplified fragment with the total size of 4311 bp by this pair of primers is consisted of those parts: 124 bp upstream sequence of the BamHI digestion site, 1321 bp promoter sequence, 2321 bp sequence of leader region plus exon plus intron , 272 bp 3'-UTR sequence, followed by 288 bp genome sequence (including the 7 bp BstEII recognition site and 5 bp protection base). The amplified fragments was then ligated to TA vector (Takara) by T4-DNA ligase of bacteriophage for further repeated sequencing analysis (Perkin Elmer AMI 377, Shanghai GeneCore) and the obtained clones that were confirmed to contain the correctly amplified exons were then selected and cut off from the TA vector by both BamHI and BstEII(Takara) enzymes. This double-enzyme digested fragment was then ligated to the genetic transformation vector pCAMBIA1301, which was cut by the same pair of enzymes. After that, choose the correct insertion-containing plasmid and introduce it into the EHA105 strains of *Agrobacterium tumefaciens* by electroporation method. Use the resulted positive EHA105 strain to transform the 8077S genome for complementary confirmation of the biological functions of the cloned Cyp81A6 gene. The transformed calli were screened in the selection medium complemented with 50 mg/L hygromycin (ABI, USA) for three rounds and then with 4.2 μM/L Bensulfonyluron-methyl (Sigma) (FIG. 6). The positive calli resistant to both selection agents were then transferred onto regeneration medium supplemented with 50 mg/l hygromycin for green seedling differentiation. The regenerated green plantlets were then subjected to the PCR analysis and the positive ones identified with the transgene were then further verified by the bentazon test at a concentration of 1250 mg/l. As a result, all the transformants recovered the resistance to bentazon (FIG. 7 shows the result of one of the plants). These results thus confirmed that the cloned Cyp81A6 was indeed to have function of resistance to both bentazon and sulfonylurea herbicides.

2.5 Structure Characteristics of the Cyp81A6

Figure 8:
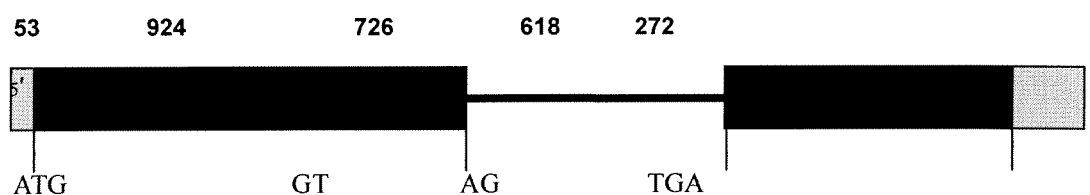
FIG. 8. Structure of Cyp81A6 gene. Black rectangle: exon of the gene; grey rectangle: 5'- and 3'-UTR of the gene; real line in the middle: intron of the gene. Their lengths are marked on top of the figure respectively. Those marked at the bottom of the figure are the initiation codon ATG, termination codon TGA as well as splice point sequences GT and AG.

The structure features of Cyp81A6 include: the 5-UTR of 53 bp prior to the translation initiation codon (the sequence from 1896 to 194 8 bp as shown in SEQ ID NO.1), the coding region of 2268 bp (the sequence from 1949 to 4216 bp as shown in SEQ ID NO.1), and the 3'-UTR of 272 bp after the termination codon (the sequence from 4217 to 4488 bp as shown in SEQ ID NO.1). The coding region of this gene is composed of two exons plus one intron (see FIG. 8). The length of two exons is 924 bp (the sequence from 1949 to 2872 bp as shown in SEQ ID NO.1) and 618 bp (the sequence from 3599 to 4216 bp as shown in SEQ ID NO.1), respectively. The length of the intron is 726 bp (the sequence from 2873 to 3598 bp as shown in SEQ ID NO.1).

The Cyp81A6 encodes a novel cytochrome P450 protein (see SEQ ID. NO.3 for its sequence). It has four conserved domains shared by the majority of P450 proteins, namely the heme-binding domain of Phe-x-x-Gly-x-Arg-x-Cys-x-Gly which is located at C-terminal. The I helix of Ala/Gly-Gly-x-Asp/Glu-Thr-Thr/Ser located at 150 amino acid residues upstream of heme-binding domain and this conserved domain plays an important role in oxygen activation. The meander area of Pro-Glu/Asp-Arg/His-Phe/Trp located between the heme-binding domain and I helix and the proline-rich hinge located at the N-terminal (Werch-Reichhart etc., 2000). In fact, it is just because of existence of these conserved domains the conservative tri-dimensional structures of the majority of cytochrome P450 proteins was capable to be maintained.

Example 2

The Targeted Mutation and Genetic Improvement of Rice Wx Gene

Two wild-type alleles Wxa and Wxb in rice cultivars are widely distributed on the Wx locus. Among which, Wxa is the feature of indica type rice and its expression activity on the RNA and protein level is 10 times stronger than the Wxb's. Its high level of expression results in high amylose content and makes the cooked rice hard and loose with a bad taste. While Wxb mainly exists in the japonica rice. Its low level of expression results in typical japonica-type amylose content at a middle level. Its rice after cooking is usually soft and delicious. The previous investigation indicated that the major difference between these two alleles of Wxa and Wxb on the expressive activity is that there is a G to T substitution in the 5'-splicing site of the leading intron of the latter (Cheng Shijun etc. 2001). This substitution results in decrease of splicing efficiency of the leading intron in the pre-mRNA of Wxb, and thus causes the reduction of amount of both mature mRNA and its translated granule-bound starch synthas (GBSS). This finally reflects by the reduction of synthesis amount of the amylose.

Based on the sequence flanking the 5' splicing site of leading intron of Wx gene and the sequence flanking the single base deletion of Cyp81A6, separately design muton molecule that can mutate the G base of the Wx splicing site (see FIG. 9 RCO1) and repairer molecule that can repair single-base deletion mutant of cyp81A6-1 (see FIG. 10 RCO2). Use the particle gun to co-introduce them into the genome of 8077S mutant simultaneously according to ratio of 1 repairer: 3 mutants. Use the sulfonylurea herbicide to screen the repairer of the cyp81A6-1 single-base deletion mutant and the co-modified mutant of wild Wx gene. After that, use the designed specific primers (forward primer: 5'-CTCTCTC ACCATTC-CTTCAG-3'(SEQ ID NO: 42), reverse primer: 5'-AGC-CTAACCAA ACATAACGA-3') (SEQ ID NO: 43) to conduct the PCR amplification followed by AccI (Takara) enzyme digestion analysis of the target sequence of the co-modified mutant. The results confirmed the successful mutation of Wx gene. Based on this, a new line with the mutated Wx gene was capable to develop through homozygous selection followed by the field test.

Example 3

Use the Double RCOs-mediated Co-modification Technology to Investigate the Biological Function of Rice Cyp8 A5, Cyp81A7 and Cyp81A8 and Other Unknown Genes In theory, the gene targeted modification technology is precisely proceeded to aim at target gene locus. As it is known that, the encoded products of Cyp81A5, Cyp81A7 and Cyp81A8 genes are a category of cytochrome P450 monooxygenase proteins and the rice P450 is a huge gene family. For instance, only one subspecies of indica type rice has 454 p450 family members. This gene family possesses a highly conserved heme binding motifs (F—X—X-G-X—R—X—C—X-G) on the protein sequence, especially their core residue of cystine, which is already confirmed to be an extremely important determinant to the biological function of the P450 gene. Therefore, it can be used as an ideal mutation target.

From the existing rice P450 database, it is clear that the amino acid sequences of the heme binding domain of rice CYP81A5, CYP81A7 and CYP81A8 and other three cytochrome P450 are FGMGRRRCPGETLA (SEQ ID NO: 44), FGMGRRK CPGETMA (SEQ ID NO: 45), and FGMGR RRCPGEMLA (SEQ ID NO: 46), respectively. Based on the nucleotide sequence and Cyp81A6 single base deletion mutation sequence information of these motif, we designed a muton molecule that could make mutation of the codon for the key amino acid residue of cystine (C) or other residues of the motif (see FIG. 11 RCO 3 and FIG. 2 RCO 4)and the repairer molecule that could carry on the repair for the single base deletion of cyp81A6-2 (see FIG. 13 RCO5). Use the particle gun to co-introduce them into the genome of Norin8m mutant simultaneously according to the ratio of 1 repairer: 3 mutons or so. Apply the sulfonylurea herbicide in the selection medium to screen the repairer of cyp81A6-2 single-base deletion mutant and the co-modifier of wild-type Cyp81A5, Cyp81A7 and Cyp81A8. After that, confirm the repairer and modifier by specific-primer-mediated PCR analysis and sequencing test of their target DNA sequence. Compare the differences of phenotypes or biochemitypes between positive co-modifier of Cyp81A5, Cyp81A7 and Cyp81A8 with the wild-type and deduce their biological functions.

In the above experimental procedures, the purpose of conducting repair at the cyp81A6-2 single base deletion locus is to provide an indirect selection for the mutation of other genes. Therefore, theoretically speaking, as long as a genetic locus such as sulfonylurea target enzyme acetolactate synthase (ALS) (Okuzaki and Toriyama 2004), which is capable for selection after modification, can be used for this purpose as the modification target.

Example 4

Figure 15:
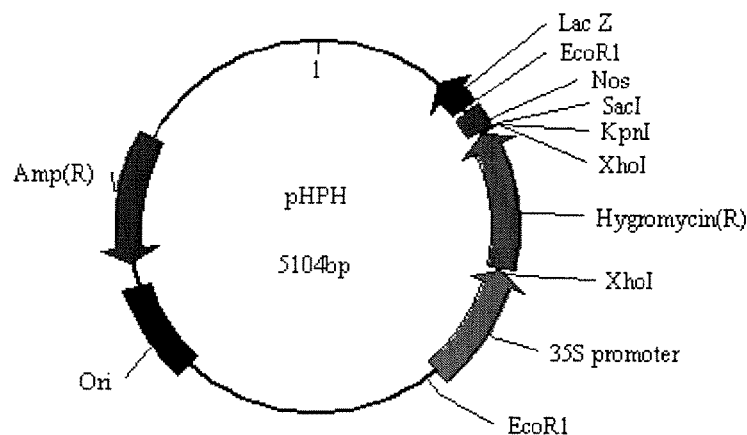
FIG. 15. The pHPH plasmid map which carries hygromycin phosphotransferase gene.

Studies on Biological Function of the Unknown P450 Genes in Rice with the Aid of Selection Effect of Exogenous Marker Gene and Modification Effect of RCOs Molecule The exogenous selectable marker gene such as anti-antibiotic marker gene, bioluminescence or chemiluminescence marker gene, carbon source metabolism key enzyme gene, herbicide resistant gene originating from bacteria, animal or other plants and GUS reporter gene etc. can provide selection effect to the mutant of target gene modified by co-introduced RCOs with them. Here we present a case study in which using hygromycin phosphotransferase (hph) gene as selectable marker. Design a RCOs molecule to target a P450 gene with unknown function (see FIG. 14 RCO6) and at the same time ligate the selectable hph gene into plasmid vector to generate a expression construct, namely pHPH (see FIG. 15). Then use the conventional particle bombardment mediated co-transformation method (Tu et al, 1998) to co-introduce both of these plasmid pHPH and RCOs into the recipient genome, and indirectly select the RCO modified P450 mutant based on the hygromycin resistance expressed by the co-introduce hph gene. Afterwards, confirm the hph transgene and the p450 putative mutants by specific-primer-mediated PCR analysis and sequencing test of the relative target DNA sequence. Compare the phenotypes or biochemical differences between the confirmed p450 mutants with the wild-type and deduce their biological functions.

Example 5

The Impression Effects of Anti-sense RNA Against the Rice Endogenous Bel Gene

Figure 16:
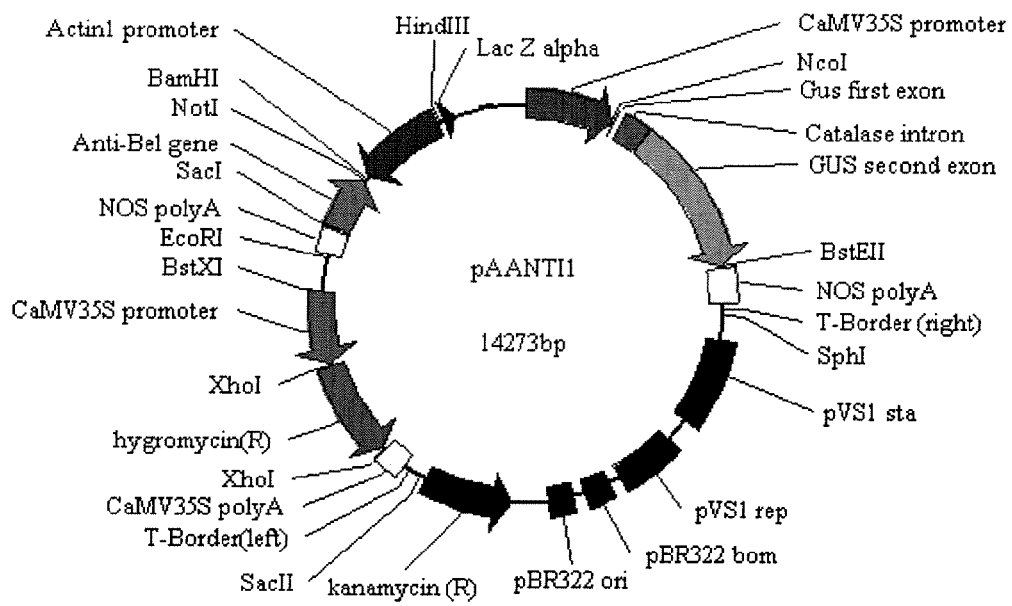
FIG. 16. pAANTI1 plasmid structural map of Cyp81A6 antisense RNA driven by Actin I promoter.
Figure 17:
FIG. 17. PCR confirmation results of Cyp81A6 antisense RNA-transformed plant originally derived from Minghui 63 restorer line. M: DL2000 (Takara) molecule weight marker; 1-2: transgenic plant; 3: wild-type control plant; 4: plasmid control.
Figure 18:
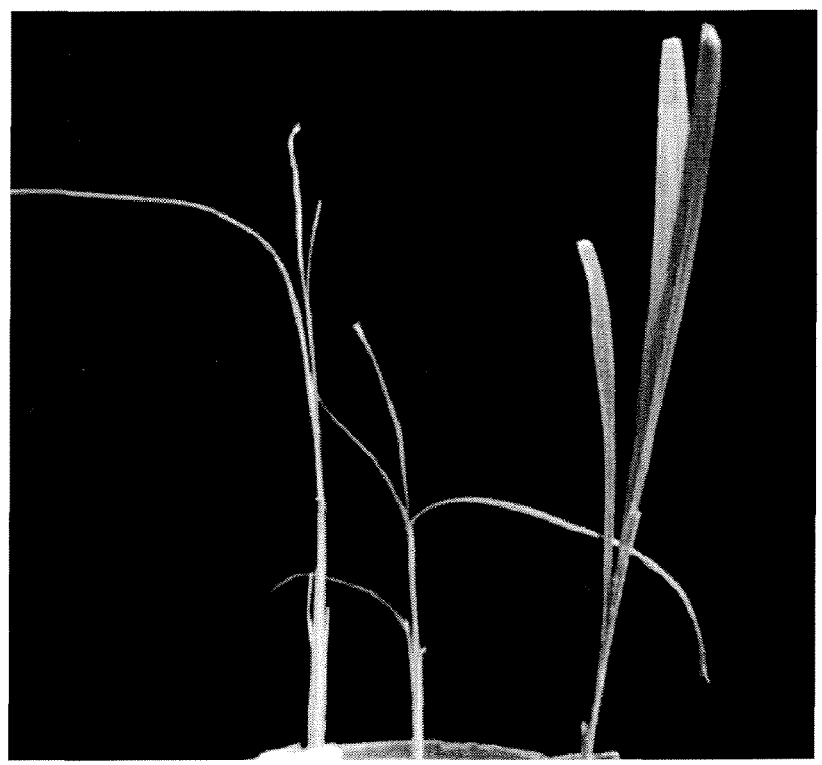
FIG. 18. The bentazon test results of Cyp81A6 antisense RNA transformed plant originally derived from Minghui 63 restorer line. Left: negative control of bentazon sensitive mutant; middle: antisense RNA-transformed plant; right: positive control of wild-type Minghui 63. The applied concentration of bentazon treatment is 1250 mg/L.

Design anti-sense RNA (RNAi) sequences (see the 1939th to 2439th nucleotide sequence of SEQ ID NO.1) in according with the coding sequence of the cloned rice Cyp81A6 gene. Fuse these antisense RNA (RNAi) sequence to the rice constitutive expression promoter such as Actin1 and then insert them into the binary vectors of pAANT11 (see FIG. 16). Use this vector to transform wild-type rice such as Minghui 63 using the modified procedures of *Agrobacterium*-mediated transformation method. After that, use the specific primers to carry on the PCR amplification analysis of transgenic TO generation plants for molecular confirmation. The results revealed that all of transgenic plants presented the fragments in according with those detected in the plasmid control lane, this thus confirming integration of the exogenous antisense RNA fragment into recipient genome of Minghui 63 (see FIG. 17). Furthermore, for phenotype confirmation, we use 1250 mg/L of bentazon to smear the leaves of the PCR positive transgenic plants (3 pieces of leaf/plant). All of the treated leaves and plants were faded and died 36 hours later (see FIG. 18). These results verified that antisense RNA was indeed to effectively impress the expression of the rice endogenous Bel gene.

Example 6

Figure 19:
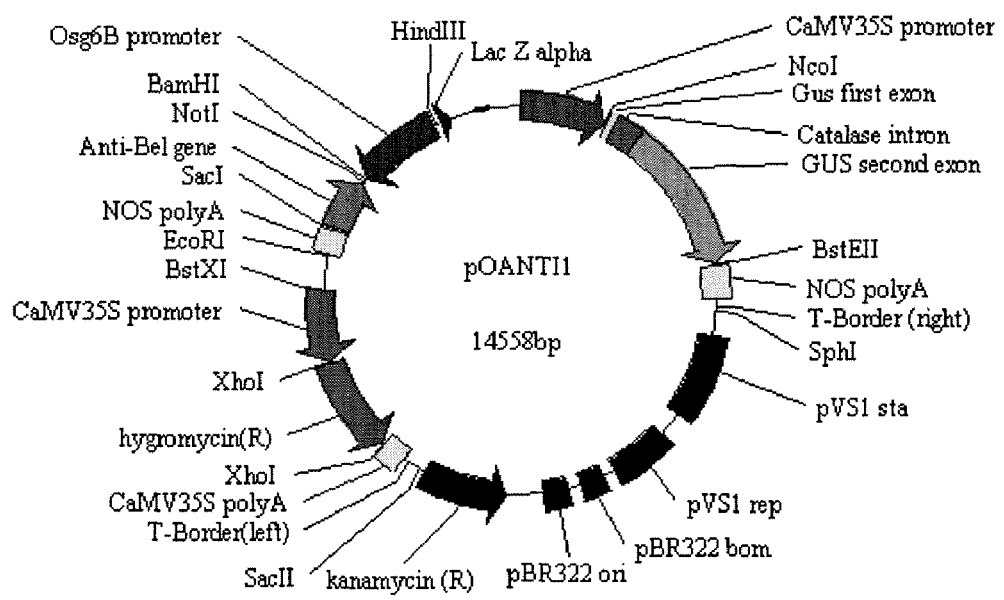
FIG. 19. pOANTI1 plasmid structural map of Cyp81A6 antisense RNA driven by the tissue specific promoter Osg6B.

Development of Chemically Supplemented Emasculation and Thermo-sensitive Male Sterile Line Fuse the antisense RNA fragments that their impression effects were confirmed effective to the rice tapetal and pollen specific expression promoter such as Osg6B or RA39 and then insert them into the binary vectors (see FIG. 19). Afterwards, use this vector to transform the photoperiod- and thermo-sensitive genic male sterile line Peiai 64S that has been widely used in rice production in China at present using the modified procedures of *Agrobacterium*-mediated co-transformation method. Let this antisense RNA to specifically inhibit the expression of the endogenous Cyp81A6 gene in the tapetal cell and pollen grain of thermo-sensitive male sterile line. On this base, it is able to develop the novel chemically supplemented emasculation and thermo-sensitive male sterile line through strict pure line selection and field test. Applying this novel male sterile line in the hybrid seed production, the mixed selfing seeds caused by unusual low midsummer temperatures can be easily examined after germination and their-derived seedlings when grown in the seedling bed can be completely killed by simply spraying sulfonylurea herbicide. The purpose of the male sterile line selfing seeds removing and its hybrid seed purity ensuring is thus reached.

Example 7

Exploitation and Application of a New Category of Herbicide-resistant Selectable Marker Fuse the entire or just coding sequence of the bentazon and sulfonylurea herbicide resistant gene Cyp81A6 to the constitutive expression promoter such as CaMV35S, Ubi-1, Actin 1 etc and the nos terminator and insert the recombinant DNA sequence into the binary vectors to replace the currently commonly used hygromycin or kanamycin resistant gene or GUS reporter gene etc. Introduce this recombinant resistant gene into the genome of 8077S, a bentazon and sulfonylurea herbicide-sensitive male sterile parental line of two-line hybrid rice. The resulted transgenic calli can continue to grow on the culture medium supplemented with sulfonylurea herbicide of BSM (on the left of FIG. 6), while the non-transgenic calli derived from wild type rice stop to grow on such culture medium (on the right of FIG. 6). These results indicate that the Cyp81A6 is capably used as selectable marker gene.

Example 8

Development of Bentazon and Sulfonylurea Herbicide Resistant Transgenic Plant

Fuse the entire sequence of the bentazon and sulfonylurea herbicide resistant gene Cyp81A6 to the constitutive expression promoter such as 35S, Ubi-1, Actin1 etc and the nos terminator and insert this recombinant DNA sequence into the binary vector, which was further transformed into the *Agrobacterium* strain. Directly use the resulted *Agrobacterium* strain and chemicals of sulfonylurea herbicide for genetic transformation and resistant callus selection. The transgenic plant that is verified by molecular analysis and phenotypic characterization can be developed into bentazon and sulfonylurea herbicide resistant transgenic line through strict pure line selection and field test. Introduction of the entire sequence of CYP81A6 gene into the mutant genome of 8077S could obtain transgenic new line highly resistant against bentazon and sulfonylurea herbicide (on the left of FIG. 7).

Example 9

Isolation of Cyp81A6 Analog/s from Genome of Other Crops or Plant Species

There are four conservative motifs or domains among different members of cytochrome P450 gene family in plant genomes, these including heme-binding domain which plays a key role to catalysis, the N-terminal hydrophobic regions important to membrane binding, the proline/glycine-rich area responsible for the correct assembling of protein, and I helix of 150 amino acid residues located at the upstream of heme binding region (Werch-Reichhart etc., 2000). Therefore, the designated specific primers based on these highly conserved region (such as forward direction primer: 5'-GCAGGAA CAGAGACAACC-3'(SEQ ID NO: 47), reverse direction:

5'-CACCTCCGCCT CCCCATC-3') (SEQ ID NO: 48) is possibly used to amplify the genome of gramineae or legume except for rice to isolate the core sequences with high homology. Then, based on this, isolate the 5'- and 3'-end flanking sequences around this core fragment by means of 5'- and 3'-RACE. So up to here, the full length sequence of the target gene that has high homology to that of rice P450 gene/s and originated from other species or family is isolated.

REFERENCES

1. Zhang Jiwen, Wu Xiaozhi. Chinese Rice Science, 1999,13 (2):65-68.
2. Zhang Jiwen, Wu Xiaozhi, Tan Lubin. Weed Science 2001, 21: 2-5.
3. Cheng Shijun, Ge Hongfei, Wang Zhongyang, Hong Mengming. Plant Physiology Journal, 2001, 27(5):381-386.
4. Liu Qiuhua and Lu Zuomei. Nanjing Agricultural University Journal, 2004, 27(4): 17-19.
5. Barcelo P, Hagel C, Becker D, Martin A, Lorz H. Plant J, 1994, 4:583-592.
6. Breitler J C, Meynard D, Legavre T, Guiderdoni E. Theor Appl Genet, 2002, 104:709-719.
7. Cai X L, Wang Z Y, Xing Y Y, Zhang J L, Hong M M. Plant J, 1998, 14(4):459-65.
8. Deng F and Hatzios K K. Pestic Biochem Physiol, 2003, 74:102-115.
9. Didierjean L., Gondet L., Perkins R., Lau S. C., Schaller H., O'Keefe D. P., and Werck-Reichhart D. E. Plant Physiol, 2002, 130:179-189.
10. Frances H, Bligh J, Larkin P D, Roach P S, Jones C A, Fu H, Park W D. Plant Mol Biol, 1998, 38(3):407-15.
11. Haack A. E. and Balke N. E. in "Abstract of the 8th IUPAC Congress of Pesticide Chemistry", 1994, 2:839.
12. Hirano H Y, Eiguchi M, Sano Y. Mol Biol Evol, 1998, 15(8):978-87.
13. Isshiki M, Morino K, Nakajima M, Okagaki R H, Wessler S R, Izawa T, Shimamoto K. Plant J, 1998, 15(1):133-8.
14. Kren B T, Cole-Strauss A, Kmiec E B, Steer C J Hepatology, 1997, 25:1462-1468.
15. Kren B T, Metz R, Kumar R, Steer C J. Semin Liver Dis, 1999, 19:93-104.
16. Lamb S. B., Lamb D. C., Kelly S. L., Stuckey D. C. FEBS Letters, 1998, 431:343-346.
17. McCouch S. R., Kochert G., Yu Z., Wang Z., Khush G. S., Coffman W. R., Tanksley. S. D. Theor Appl Genet, 1988, 76:815-829.
18. Mori T. Jpn J Breed, 34(suppl.1): 1984, 421-422.
19. Pierrel M. A., Batard Y., Kazmaier M., Mignotte-Vieus C., Durst F., and Werck-Reichhart D. Eur. J. Biochem., 1994, 224(3):835-44.
20. Sano, Y., Katsumata M., and Amana E. SABRAO J., 1985, 17:121-127.
21. Siminszky B., Corbin F. T., Ward E. R., Fleischmann T. J., and Dewey R. E. Proc. Natl. Acad. Sci. USA, 1999, 4: 1750-1755.
22. Tu J, Ona I, Zhang Q, Mew T W, Khush G S, Datta S K. Theor Appl Genet, 1998, 97:31-36.
23. Vidal J R, Kikkert J R, Wallace P G, Reisch B I. Plant Cell Rep., 2003, 22:252-260.
24. Wang, Z., Zheng F., Shen G., Gao J., Snustad D. P., Li M., Zhang J., and Hong M. Plant J., 1995, 613-622.
25. Werch-Reichhart D, Hehn A, Didierjean L. Trends in Plant Sci, 2000, 5(3):116-123.
26. Yamada T., Kambara Y., Imaishi H., and Ohkawa H. Pestic. Biochem. Physiol., 2000, 68: 11-25.
27. Yoon K, Cole-Strauss A, Kmiec E B. Proc Natl Acad Sci USA, 1996, 93:2071-2076.
28. Zhu T, Mettenburg K, Peterson D J, Tagliani L, Baszcynski C L. Nat Biotechnol, 2000, 18:555-558.

The invention claimed is:

1. A method for making a transformed plant comprising the steps of introducing an isolated bentazon and sulfonylurea herbicide resistant gene into a plant cell and selecting for resistance to a bentazon and sulfonylurea herbicide, wherein said gene comprises a nucleotide sequence selected from the group consisting of:
   (a) a nucleotide sequence having the nucleotide sequence shown in SEQ ID NO.: 1;
   (b) a nucleotide sequence fragment or derivative thereof, which has the same function as the nucleotide sequence of position 1949 through 4216 of SEQ ID NO.: 1;
   (c) a nucleotide sequence having the nucleotide sequence shown in SEQ ID NO.: 2;
   (d) a nucleotide sequence fragment or derivative thereof, which has the same function as the nucleotide sequence of position 54 through 1595 of SEQ ID NO.: 2; and
   (e) a nucleotide sequence that can hybridize with the nucleotide sequence shown in SEQ ID NO.: 1 or SEQ ID NO.2 under stringent conditions.

2. The method of claim 1, wherein said gene comprises the nucleotide sequence shown in SEQ ID NO.: 1 or SEQ ID NO.: 2.

3. A method for making a transformed plant comprising the step of introducing a recombinant vector comprising the nucleotide sequence as defined in claim 2 into a plant cell, and selecting for resistance to bentazon and sulfonylurea herbicides.

4. The method of claim 1, wherein said nucleotide sequence is in a recombinant vector, and wherein the recombinant vector comprises regulatory elements essential for transcription of said nucleotide sequence.

5. The method according to claim 4, wherein said nucleotide sequence is operatively linked to the transcriptional regulatory elements.

6. The method according to claim 4, wherein said regulatory elements essential for transcription comprise promoter, terminator, enhancer, MAR sequence or 5' upstream regulatory sequence.

7. The method according to claim 4, wherein said vector is an expression vector.

8. A method for developing a chemically supplemented emasculation and thermo-sensitive male sterile plant comprising the steps of introducing a recombinant nucleic acid molecule into the thermo-sensitive male sterile plant, wherein said recombinant nucleic acid molecule comprises antisense RNA or RNAi fragments of the gene recited in claim 1, to inhibit expression of the gene in anthers, and contacting the plant with a sulfonylurea herbicide to kill pollen, thereby creating a chemically supplemented emasculation and thermo-sensitive male sterile plant.

9. An isolated bentazon and sulfonylurea herbicide sensitive gene, which comprises a nucleotide sequence selected from the groups consisting of:
   (a) a nucleotide sequence obtained by deleting the 2455th base C or 4006th base G from the nucleotide sequence shown in the SEQ ID NO.: 1; and
   (b) a nucleotide sequence obtained by the deleting the 560th base C or 1385th base G from the nucleotide sequence shown in the SEQ ID NO.: 2.

10. A genetically modified plant cell, which comprises the gene as defined in claim 9.

11. A recombinant nucleic acid molecule comprising antisense RNA or RNAi fragments, wherein said antisense RNA or RNAi fragments comprise the nucleotide sequence as defined in claim 9.

12. A method for making a transformed plant comprising the step of introducing the isolated bentazon and sulfonylurea herbicide sensitive gene of claim 9 into a plant cell and selecting for sensitivity to a bentazon and sulfonylurea herbicide.

* * * * *

UNITED STATES PATENT AND TRADEMARK OFFICE
CERTIFICATE OF CORRECTION

PATENT NO.       : 8,049,063 B2                                     Page 1 of 1
APPLICATION NO.  : 11/993990
DATED            : November 1, 2011
INVENTOR(S)      : Tu et al.

It is certified that error appears in the above-identified patent and that said Letters Patent is hereby corrected as shown below:

On the Title Page, in item (73), under "Assignees", in Column 1, Line 3, delete "Wuhun (CN)" and insert -- Wuhan (CN) --, therefor.

Signed and Sealed this
Nineteenth Day of August, 2014

Michelle K. Lee
*Deputy Director of the United States Patent and Trademark Office*

SEQUENCE LISTING

```
<160> NUMBER OF SEQ ID NOS: 48

<210> SEQ ID NO 1
<211> LENGTH: 4575
<212> TYPE: DNA
<213> ORGANISM: Artificial Sequence
<220> FEATURE:
<223> OTHER INFORMATION: Synthetic polynucleotide
<220> FEATURE:
<221> NAME/KEY: 5'UTR
<222> LOCATION: (1896)..(1948)
<220> FEATURE:
<221> NAME/KEY: gene
<222> LOCATION: (1949)..(4216)
<220> FEATURE:
<221> NAME/KEY: Intron
<222> LOCATION: (2873)..(3598)
<220> FEATURE:
<221> NAME/KEY: 3'UTR
<222> LOCATION: (4217)..(4488)

<400> SEQUENCE: 1
cggttggagg tggcggagca ctggtaccga ctctacaaga cggacaatca acgggtacca      60
caatccggct ccacctcgac gcgattgcgg caaccacgaa aacctcacgc tccaatctgt     120
gccctccgcc cgtgctcgct gcatctcgtg ccaccgtctc ggactctcga tcctcatggc     180
ctgaattatc ctaattcttc gttaccagtt tttttgagac taatatgact cccatcaaac     240
aatgcagttg agagtgagtt cttacctgta ttatatagta cattgtattt aaaccatagt     300
```

```
acatggggac agtggtgcgt tcatcaattt atggattgtg gtaggctggt agctgtttga    360
tttgtcacta aaattgcacg acgacaacac tttggccctg tttagattct aacttttttc    420
ttcaaacttc caacttttcc gtcacatcga acttttctac acacacaaac ttccaacttt    480
cccgtcacct tcactttagg ttcctaagtt taggttacct tcactttagg ttcctaaatt    540
tatcactaag tctgaaattt atccctaaac caaaatacca ggtacaacgg atccctcaat    600
ctacaaaact caatcaccca agattgtaga tagtattatg tccggtttta actgacgtgt    660
caagttgagt taacgtggaa tctatgcggg ccccacatgt aagtggctag tactttttc     720 cacgttggac gaaaccgtct cccaaaccac taaaggaggc gatatgcacc gattttgata    780 gatggggag acgttatacc ctgttttatt atcaagagat gtgattcaac caggagcaag     840
agttgagaga gcaagaatag acttattcgt gagcccacag gctaaacccg ccacggccca    900
cagactaagc ccgccaactc gggccgttcg gcccagtttg cacgcatggt gggccggaaa    960
ctggaatctc cgaaccgcaa cggaatcgac gacatctgta gccacagcgc gcactcgacg   1020
gcgggcagct tcgtcactgg ttcgagctgt ctgctgactc aacgacgaac acacgtactc   1080
ctgctcggtt tcttcctccg tgtcgcacaa aagtcaaatt gctctctatt agtattcatt   1140
attagcactt caaaccttc tttacgtttt aaacgaacca actaatcagg ttatgaggac    1200
tataataatc gaatccaggg atcttgctgg aagcaattga ataatcgccc aacgattgag   1260
ttcatttctt gtctccaaag ctgtctcctg atagtcaaca ggtctcggtc ctcgcagagt   1320
cgcactgcga tttggcctct ggaaactgga agagatctc gatccaccac aagaaaatgc    1380
caagcagcac gacgacgaag acgacaacgc cttccaggta cgtagcaatt gaatacggaa   1440
tactctctcc gttaaaaacg tttgattatt ttcctaatca aactttatca tgtttgacca   1500
aatttataga aaaaaataac aacatcttaa atataaaatt agtataacta aatctagcat   1560
tggatatact ttcataatat ttgtttgttt tatgttaaaa atactactat attttctat    1620 aagcttagtc aaatttaaat caaattaaag aagattaatt agaaaaatag ccaaacgatt   1680
tgtaatatgc aacggagtga gtagaagtaa tcgcccagcc tcgccaacga ggcaacgaga   1740
cccgtaatgc aacgatcgca tctgcgtttc aggcgtcagc catggcgtct gcagagatgc   1800
ctggattgtc tccgcaagat ctgatccatt tcatctcctt ctagaagcac aagcgccgct   1860
cggtataaag gcagacgcat tgtcacaaat agctgcagtg caccagagtc acagaaacac   1920
atcacacatt cgtgagctca gcttagccat ggataacgcc tacattattg ccattctctc   1980
tgtagctatc ctcttcttgc tccactacta cctcctcggc cgcggcaatg gcggggcggc   2040
gcggctgccg ccgggtccac cggccgtccc gatcctggga cacctccacc tcgtcaagaa   2100
gccgatgcac gccaccatgt cccgcctcgc cgagcggtac gggccggtgt tctcgctgcg   2160
cctcgggtcg cggcgcgccg tggtggtgtc gtcgccgggg tgcgccaggg agtgcttcac   2220
cgagcacgac gtgaccttcg cgaaccggcc caggttcgag tcgcagctgc tggtctcgtt   2280
caacggcgcc gcgctcgcca cggcgagcta cggcgcgcac tggcgcaacc tccgccggat   2340
cgtcgccgtg cagctgctct ccgcgcaccg cgtcggcctc atgtcggggc tcatcgccgg   2400
cgaggtccgc gccatggtgc ggaggatgta ccgcgccgcg gccgcgtccc ccgccggcgc   2460
cgcgcgcatc cagctgaagc ggaggctgtt cgaggtctcc ctcagcgtgc tcatggagac   2520
catcgcccac accaaggcga cccgccccga cggacccg gacaccgaca tgtccgtgga     2580
agcccaggag tttaagcagg tcgtcgacga gatcatcccg cacatcggcg cggccaacct   2640
gtgggactac ttgccggcgc tccggtggtt cgacgtgttc ggcgtcagga ggaagatcct   2700
```

-continued

```
cgccgctgta agccggaggg acgcgttcct tcgccgcctg atcgacgcgg agcggcggag    2760
gctggacgac ggcgacgagg gcgagaagaa gagcatgatc gccgtgctgc tcactctgca    2820
gaagacagag ccggaggtgt acaccgataa catgatcaca gctctaacgg cggtgagttc    2880
atcttctgct gttttacctt tctgatatct gaattctctc attggtgcgt aattttttt     2940 ttttggctgt catcggtata gctttcttaa gcactcagta gccttgcaat tataaaaga    3000 aaaacaatca gtagctttt acatgctttg agtcagtcag tagcagtgtg gcactatcag    3060
cattcagcag tattcatgtt gtttgctaat cactatcatg gtttgagtca gcacaatcag    3120
tagcttttga catggtttga gtcagcagta tcttttctag gaactgaatt agttattcat    3180
ttagtacaac ttgtttgtct gtctattgat tgctttaaat tatttcttct atgcaaccct    3240
ctaatcctag tatagtacta gccttttata tgaagaatca tcaataattt tcttctcact    3300
ttcagtgtag cttacttaa tgaatattt gaaagatcgc ctagttgcct tattataatt    3360
gtataaaagg aaaacaatca gtagccttt acatggttga gtcagcgagt tatcaggagt    3420 actattgtt atcatggtag tagcacgata gactattcaa cccgggcgat taaaatcctt    3480
ctcccaaatt tgtattcttt gttttttcct caaaaattca ccaaactctt ggaactatta    3540
tagttcagtt ttagacaaaa aaaaatgaa atcttagttc caccctcttg ccgtgcagaa    3600
cttgttcgga gcaggaacag agacaacctc gacgacatca gaatgggcga tgtcgctact    3660
gctgaaccac cccgacacac tcaagaaagc gcaagccgag atcgacgcat ccgtcggcaa    3720
ctctcgcctg atcaccgccg acgacgtgac tcgcctcggc tacctccagt gcatcgtcag    3780
ggagacgctc cgcctgtacc ccgccgcgcc gatgctcctc ccgcacgagt cctccgccga    3840
ctgcaaggtc ggcggctaca acatcccgcg cgggtcgatg ttgctcatca acgcgtacgc    3900
catccaccgt gacccggcgg tgtgggagga gccggagaag ttcatgccgg agaggttcga    3960
ggacggcggt tgcgacggca atctcttgat gccgttcggg atggggaggc ggaggtgccc    4020
cggcgagacg ctggcgctgc gcacagtggg gttggtgctg ggcacgctga tccagtgctt    4080
cgactgggag agggtcgacg gcgtggaggt cgacatgact gaaggtggcg ggctcaccat    4140
ccccaaggtc gtgccgttgg aggccatgtg caggccgcgc gacgccatgg tggtgttctc    4200
tcgcgagctc gtctgaatat tttttggcgg cgttttgcatc tccaggacga actcatgtat    4260
tgaaagcacc aaaagtaagt agcaaataag cttctcgtga gcatacacat aacacatgtg    4320
agcttgtaat gtggaataaa ttacacgtag aggatttgga agagagtgac tgcgctagca    4380
atcgctcttt gagagttgtg ttttacagtt ttagtgagga accaatttgt atgaatgtgc    4440
aataatcatg tataaagtat aattgtacac gccaggtatt tcaatttcat attgcttgtg    4500
tgatgtatgc gttcgaatac tatacagtca acaaaagaga acaaaattac tatgagctta    4560
tacgaccagt gttca                                                    4575
```

```
<210> SEQ ID NO 2
<211> LENGTH: 1867
<212> TYPE: DNA
<213> ORGANISM: Artificial Sequence
<220> FEATURE:
<223> OTHER INFORMATION: Synthetic polynucleotide
<220> FEATURE:
<221> NAME/KEY: 5'UTR
<222> LOCATION: (1)..(53)
<220> FEATURE:
<221> NAME/KEY: CDS
<222> LOCATION: (54)..(1595)
<220> FEATURE:
<221> NAME/KEY: 3'UTR
```

<222> LOCATION: (1596)..(1867)

<400> SEQUENCE: 2

```
gagtgcacca gagtcacaga aacacatcac acattcgtga gctcagctta gcc atg            56
                                                              Met
                                                               1 gat aac gcc tac att att gcc att ctc tct gta gct atc ctc ttc ttg           104
Asp Asn Ala Tyr Ile Ile Ala Ile Leu Ser Val Ala Ile Leu Phe Leu
         5                  10                  15 ctc cac tac tac ctc ctc ggc cgc ggc aat ggc ggg gcg gcg cgg ctg           152
Leu His Tyr Tyr Leu Leu Gly Arg Gly Asn Gly Gly Ala Ala Arg Leu
     20                  25                  30 ccg ccg ggt cca ccg gcc gtc ccg atc ctg gga cac ctc cac ctc gtc           200
Pro Pro Gly Pro Pro Ala Val Pro Ile Leu Gly His Leu His Leu Val
 35                  40                  45 aag aag ccg atg cac gcc acc atg tcc cgc ctc gcc gag cgg tac ggg           248
Lys Lys Pro Met His Ala Thr Met Ser Arg Leu Ala Glu Arg Tyr Gly
 50                  55                  60                  65 ccg gtg ttc tcg ctg cgc ctc ggg tcg cgg cgc gcc gtg gtg gtg tcg           296
Pro Val Phe Ser Leu Arg Leu Gly Ser Arg Arg Ala Val Val Val Ser
                 70                  75                  80 tcg ccg ggg tgc gcc agg gag tgc ttc acc gag cac gac gtg acc ttc           344
Ser Pro Gly Cys Ala Arg Glu Cys Phe Thr Glu His Asp Val Thr Phe
             85                  90                  95 gcg aac cgg ccc agg ttc gag tcg cag ctg ctc gtc tcg ttc aac ggc           392
Ala Asn Arg Pro Arg Phe Glu Ser Gln Leu Leu Val Ser Phe Asn Gly
         100                 105                 110 gcc gcg ctc gcc acg gcg agc tac ggc gcg cac tgg cgc aac ctc cgc           440
Ala Ala Leu Ala Thr Ala Ser Tyr Gly Ala His Trp Arg Asn Leu Arg
     115                 120                 125 cgg atc gtc gcc gtg cag ctg ctc tcc gcg cac cgc gtc ggc ctc atg           488
Arg Ile Val Ala Val Gln Leu Leu Ser Ala His Arg Val Gly Leu Met
 130                 135                 140                 145 tcg ggg ctc atc gcc ggc gag gtc cgc gcc atg gtg cgg agg atg tac           536
Ser Gly Leu Ile Ala Gly Glu Val Arg Ala Met Val Arg Arg Met Tyr
                 150                 155                 160 cgc gcc gcg gcc gcg tcc ccc gcc ggc gcc cgc atc cag ctg aag           584
Arg Ala Ala Ala Ala Ser Pro Ala Gly Ala Arg Ile Gln Leu Lys
             165                 170                 175 cgg agg ctg ttc gag gtc tcc ctc agc gtg ctc atg gag acc atc gcc           632
Arg Arg Leu Phe Glu Val Ser Leu Ser Val Leu Met Glu Thr Ile Ala
         180                 185                 190 cac acc aag gcg acc cgc ccc gag acg gac ccg gac acc gac atg tcc           680
His Thr Lys Ala Thr Arg Pro Glu Thr Asp Pro Asp Thr Asp Met Ser
     195                 200                 205 gtg gaa gcc cag gag ttt aag cag gtc gtc gac gag atc atc ccg cac           728
Val Glu Ala Gln Glu Phe Lys Gln Val Val Asp Glu Ile Ile Pro His
 210                 215                 220                 225 atc ggc gcg gcc aac ctg tgg gac tac ttg ccg gcg ctc cgg tgg ttc           776
Ile Gly Ala Ala Asn Leu Trp Asp Tyr Leu Pro Ala Leu Arg Trp Phe
                 230                 235                 240 gac gtg ttc ggc gtc agg agg aag atc ctc gcc gct gta agc cgg agg           824
Asp Val Phe Gly Val Arg Arg Lys Ile Leu Ala Ala Val Ser Arg Arg
             245                 250                 255 gac gcg ttc ctt cgc cgc ctg atc gac gcg gag cgg cgg agg ctg gac           872
Asp Ala Phe Leu Arg Arg Leu Ile Asp Ala Glu Arg Arg Arg Leu Asp
         260                 265                 270 gac ggc gac gag ggc gag aag aag agc atg atc gcc gtg ctc ctc act           920
Asp Gly Asp Glu Gly Glu Lys Lys Ser Met Ile Ala Val Leu Leu Thr
     275                 280                 285
```

```
ctg cag aag aca gag ccg gag gtg tac acc gat aac atg atc aca gct      968
Leu Gln Lys Thr Glu Pro Glu Val Tyr Thr Asp Asn Met Ile Thr Ala
290             295                 300                 305 cta acg gcg aac ttg ttc gga gca gga aca gag aca acc tcg acg aca     1016
Leu Thr Ala Asn Leu Phe Gly Ala Gly Thr Glu Thr Thr Ser Thr Thr
            310                 315                 320 tca gaa tgg gcg atg tcg cta ctg ctg aac cac ccc gac aca ctc aag     1064
Ser Glu Trp Ala Met Ser Leu Leu Leu Asn His Pro Asp Thr Leu Lys
        325                 330                 335 aaa gcg caa gcc gag atc gac gca tcc gtc ggc aac tct cgc ctg atc     1112
Lys Ala Gln Ala Glu Ile Asp Ala Ser Val Gly Asn Ser Arg Leu Ile
    340                 345                 350 acc gcc gac gac gtg act cgc ctc ggc tac ctc cag tgc atc gtc agg     1160
Thr Ala Asp Asp Val Thr Arg Leu Gly Tyr Leu Gln Cys Ile Val Arg
355                 360                 365 gag acg ctc cgc ctg tac ccc gcc gcg ccg atg ctc ctc ccg cac gag     1208
Glu Thr Leu Arg Leu Tyr Pro Ala Ala Pro Met Leu Leu Pro His Glu
370                 375                 380                 385 tcc tcc gcc gac tgc aag gtc ggc ggc tac aac atc ccg cgc ggg tcg     1256
Ser Ser Ala Asp Cys Lys Val Gly Gly Tyr Asn Ile Pro Arg Gly Ser
                390                 395                 400 atg ttg ctc atc aac gcg tac gcc atc cac cgt gac ccg gcg gtg tgg     1304
Met Leu Leu Ile Asn Ala Tyr Ala Ile His Arg Asp Pro Ala Val Trp
            405                 410                 415 gag gag ccg gag aag ttc atg ccg gag agg ttc gag gac ggc ggg tgc     1352
Glu Glu Pro Glu Lys Phe Met Pro Glu Arg Phe Glu Asp Gly Gly Cys
        420                 425                 430 gac ggc aat ctc ttg atg ccg ttc ggg atg ggg agg cgg agg tgc ccc     1400
Asp Gly Asn Leu Leu Met Pro Phe Gly Met Gly Arg Arg Arg Cys Pro
    435                 440                 445 ggc gag acg ctg gcg ctg cgc aca gtg ggg ttg gtg ctg ggc acg ctg     1448
Gly Glu Thr Leu Ala Leu Arg Thr Val Gly Leu Val Leu Gly Thr Leu
450                 455                 460                 465 atc cag tgc ttc gac tgg gag agg gtc gac ggc gtg gag gtc gac atg     1496
Ile Gln Cys Phe Asp Trp Glu Arg Val Asp Gly Val Glu Val Asp Met
                470                 475                 480 act gaa ggt ggc ggg ctc acc atc ccc aag gtc gtg ccg ttg gag gcc     1544
Thr Glu Gly Gly Gly Leu Thr Ile Pro Lys Val Val Pro Leu Glu Ala
            485                 490                 495 atg tgc agg ccg cgc gac gcc atg ggt ggt gtt ctt cgc gag ctc gtc     1592
Met Cys Arg Pro Arg Asp Ala Met Gly Gly Val Leu Arg Glu Leu Val
        500                 505                 510 tga atatttttg gcggcgtttg catctccagg acgaactcat gtattgaaag           1645
caccaaaagt aagtagcaaa taagcttctc gtgagcatac acataacaca tgtgagcttg   1705
taatgtggaa taaattacac gtagaggatt tggaagagag tgactgcgct agcaatcgct   1765
ctttgagagt tgtgttttac agttttagtg aggaaccaat ttgtatgaat gtgcaataat   1825
catgtataaa gtataattgt acacgccagg tatttcaatt tc                      1867

<210> SEQ ID NO 3
<211> LENGTH: 513
<212> TYPE: PRT
<213> ORGANISM: Artificial Sequence
<220> FEATURE:
<223> OTHER INFORMATION: Synthetic Construct

<400> SEQUENCE: 3

Met Asp Asn Ala Tyr Ile Ile Ala Ile Leu Ser Val Ala Ile Leu Phe
1               5                   10                  15

Leu Leu His Tyr Tyr Leu Leu Gly Arg Gly Asn Gly Gly Ala Ala Arg
```

```
              20                  25                  30
Leu Pro Pro Gly Pro Pro Ala Val Pro Ile Leu Gly His Leu His Leu
            35                  40                  45

Val Lys Lys Pro Met His Ala Thr Met Ser Arg Leu Ala Glu Arg Tyr
50                  55                  60

Gly Pro Val Phe Ser Leu Arg Leu Gly Ser Arg Arg Ala Val Val Val
65                  70                  75                  80

Ser Ser Pro Gly Cys Ala Arg Glu Cys Phe Thr Glu His Asp Val Thr
                85                  90                  95

Phe Ala Asn Arg Pro Arg Phe Glu Ser Gln Leu Leu Val Ser Phe Asn
                100                 105                 110

Gly Ala Ala Leu Ala Thr Ala Ser Tyr Gly Ala His Trp Arg Asn Leu
            115                 120                 125

Arg Arg Ile Val Ala Val Gln Leu Leu Ser Ala His Arg Val Gly Leu
            130                 135                 140

Met Ser Gly Leu Ile Ala Gly Glu Val Arg Ala Met Val Arg Arg Met
145                 150                 155                 160

Tyr Arg Ala Ala Ala Ser Pro Ala Gly Ala Arg Ile Gln Leu
                165                 170                 175

Lys Arg Arg Leu Phe Glu Val Ser Leu Ser Val Leu Met Glu Thr Ile
            180                 185                 190

Ala His Thr Lys Ala Thr Arg Pro Glu Thr Asp Pro Asp Thr Asp Met
            195                 200                 205

Ser Val Glu Ala Gln Glu Phe Lys Gln Val Val Asp Glu Ile Ile Pro
210                 215                 220

His Ile Gly Ala Ala Asn Leu Trp Asp Tyr Leu Pro Ala Leu Arg Trp
225                 230                 235                 240

Phe Asp Val Phe Gly Val Arg Arg Lys Ile Leu Ala Ala Val Ser Arg
                245                 250                 255

Arg Asp Ala Phe Leu Arg Arg Leu Ile Asp Ala Glu Arg Arg Leu
                260                 265                 270

Asp Asp Gly Asp Glu Gly Glu Lys Lys Ser Met Ile Ala Val Leu Leu
            275                 280                 285

Thr Leu Gln Lys Thr Glu Pro Glu Val Tyr Thr Asp Asn Met Ile Thr
290                 295                 300

Ala Leu Thr Ala Asn Leu Phe Gly Ala Gly Thr Glu Thr Thr Ser Thr
305                 310                 315                 320

Thr Ser Glu Trp Ala Met Ser Leu Leu Leu Asn His Pro Asp Thr Leu
                325                 330                 335

Lys Lys Ala Gln Ala Glu Ile Asp Ala Ser Val Gly Asn Ser Arg Leu
            340                 345                 350

Ile Thr Ala Asp Asp Val Thr Arg Leu Gly Tyr Leu Gln Cys Ile Val
            355                 360                 365

Arg Glu Thr Leu Arg Leu Tyr Pro Ala Ala Pro Met Leu Leu Pro His
            370                 375                 380

Glu Ser Ser Ala Asp Cys Lys Val Gly Gly Tyr Asn Ile Pro Arg Gly
385                 390                 395                 400

Ser Met Leu Leu Ile Asn Ala Tyr Ala Ile His Arg Asp Pro Ala Val
                405                 410                 415

Trp Glu Glu Pro Glu Lys Phe Met Pro Glu Arg Phe Glu Asp Gly Gly
                420                 425                 430

Cys Asp Gly Asn Leu Leu Met Pro Phe Gly Met Gly Arg Arg Cys
            435                 440                 445
```

```
Pro Gly Glu Thr Leu Ala Leu Arg Thr Val Gly Leu Val Leu Gly Thr
    450                 455                 460

Leu Ile Gln Cys Phe Asp Trp Glu Arg Val Asp Gly Val Glu Val Asp
465                 470                 475                 480

Met Thr Glu Gly Gly Gly Leu Thr Ile Pro Lys Val Val Pro Leu Glu
                485                 490                 495

Ala Met Cys Arg Pro Arg Asp Ala Met Gly Gly Val Leu Arg Glu Leu
            500                 505                 510

Val

<210> SEQ ID NO 4
<211> LENGTH: 20
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: Forward Primer 7a

<400> SEQUENCE: 4
gtcagagcaa ggtcggagag                                            20

<210> SEQ ID NO 5
<211> LENGTH: 20
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: Reverse Primer 7a

<400> SEQUENCE: 5
tcggtgatca ttgtcatttg                                            20

<210> SEQ ID NO 6
<211> LENGTH: 21
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: Forward primer 3a

<400> SEQUENCE: 6
tgttttcttt ttcgctgtgt g                                          21

<210> SEQ ID NO 7
<211> LENGTH: 20
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: Reverse Primer 3a

<400> SEQUENCE: 7
gcaagccttt ttgcgtattc                                            20

<210> SEQ ID NO 8
<211> LENGTH: 20
<212> TYPE: DNA
<213> ORGANISM: Artificial Sequence
<220> FEATURE:
```

```
<223> OTHER INFORMATION: Synthetic Primer
<220> FEATURE:
<221> NAME/KEY: misc_feature
<223> OTHER INFORMATION: Forward Primer 8a

<400> SEQUENCE: 8
gcttccctct ccttccactt                                               20

<210> SEQ ID NO 9
<211> LENGTH: 20
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: Reverse Primer 8a

<400> SEQUENCE: 9
cttgtgagtg agtggtgacg                                               20

<210> SEQ ID NO 10
<211> LENGTH: 20
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: P1-1a

<400> SEQUENCE: 10
gctgtgcgta tccaatgaag                                               20

<210> SEQ ID NO 11
<211> LENGTH: 19
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: P1-1b

<400> SEQUENCE: 11
tcagggagag ctcgaacag                                                19

<210> SEQ ID NO 12
<211> LENGTH: 18
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: P1-2a

<400> SEQUENCE: 12
ctcatgtcgg ggctcatc                                                 18

<210> SEQ ID NO 13
<211> LENGTH: 20
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: P1-2b
```

```
<400> SEQUENCE: 13
tagctttctc ccgattgacc                                              20

<210> SEQ ID NO 14
<211> LENGTH: 20
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: P1-3a

<400> SEQUENCE: 14
ttcatgaccc agacgaaaaa                                              20

<210> SEQ ID NO 15
<211> LENGTH: 20
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: P1-3b

<400> SEQUENCE: 15
atgagtttgc cctggagatg                                              20

<210> SEQ ID NO 16
<211> LENGTH: 20
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: P2-1a

<400> SEQUENCE: 16
tgagaagacc aaggcaggag                                              20

<210> SEQ ID NO 17
<211> LENGTH: 19
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: P2-1b

<400> SEQUENCE: 17
ggcaacaaat cgacacacg                                               19

<210> SEQ ID NO 18
<211> LENGTH: 18
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: P2-2a

<400> SEQUENCE: 18
ggctgcctcc tcctctct                                                18
```

```
<210> SEQ ID NO 19
<211> LENGTH: 20
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: P2-2b

<400> SEQUENCE: 19
tgaggatcga gagtccgaga                                              20

<210> SEQ ID NO 20
<211> LENGTH: 20
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: P2-3a

<400> SEQUENCE: 20
aataatcgcc caacgattga                                              20

<210> SEQ ID NO 21
<211> LENGTH: 20
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: P2-3b

<400> SEQUENCE: 21
ggagacaatc caggcatctc                                              20

<210> SEQ ID NO 22
<211> LENGTH: 19
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: P2-4a

<400> SEQUENCE: 22
gatcgcatct gcgtttcag                                               19

<210> SEQ ID NO 23
<211> LENGTH: 18
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: P2-4b

<400> SEQUENCE: 23
gatgagcccc gacatgag                                                18

<210> SEQ ID NO 24
<211> LENGTH: 18
<212> TYPE: DNA
<213> ORGANISM: Artificial Sequence
<220> FEATURE:
```

```
<223> OTHER INFORMATION: Synthetic Primer
<220> FEATURE:
<221> NAME/KEY: misc_feature
<223> OTHER INFORMATION: P2-5a

<400> SEQUENCE: 24
cctcatgtcg gggctcat                                                    18

<210> SEQ ID NO 25
<211> LENGTH: 21
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: P2-5b

<400> SEQUENCE: 25
cgcaccaatg agagaattca g                                                21

<210> SEQ ID NO 26
<211> LENGTH: 23
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: P2-6a

<400> SEQUENCE: 26
aaatcttagt tccaccctct tgc                                              23

<210> SEQ ID NO 27
<211> LENGTH: 19
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: P2-6b

<400> SEQUENCE: 27
tcgtcctgga gatgcaaac                                                   19

<210> SEQ ID NO 28
<211> LENGTH: 27
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: P3-1a

<400> SEQUENCE: 28
tgcgtaatac aacttactat ttccgta                                          27

<210> SEQ ID NO 29
<211> LENGTH: 18
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: P3-1b
```

```
<400> SEQUENCE: 29
gaacagcctc cgcttcag                                                   18

<210> SEQ ID NO 30
<211> LENGTH: 20
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: P3-2a

<400> SEQUENCE: 30
atggtgcaga ggatgtaccg                                                 20

<210> SEQ ID NO 31
<211> LENGTH: 24
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: P3-2b

<400> SEQUENCE: 31
ttcaaattaa gcgttcaaaa ttca                                            24

<210> SEQ ID NO 32
<211> LENGTH: 20
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: P3-3a

<400> SEQUENCE: 32 acccctttc ctctttcgtg                                                  20

<210> SEQ ID NO 33
<211> LENGTH: 20
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: P3-3b

<400> SEQUENCE: 33
gatgaagcct acctggtgga                                                 20

<210> SEQ ID NO 34
<211> LENGTH: 20
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: P4-1a

<400> SEQUENCE: 34
cctcaaggct caagcatcat                                                 20
```

-continued

```
<210> SEQ ID NO 35
<211> LENGTH: 19
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: P4-1b

<400> SEQUENCE: 35
gaacagcctc cgattcagc                                                  19

<210> SEQ ID NO 36
<211> LENGTH: 19
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: P4-2a

<400> SEQUENCE: 36
acatggtgcg gaggatgta                                                  19

<210> SEQ ID NO 37
<211> LENGTH: 21
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: P4-2b

<400> SEQUENCE: 37
tggtttctga tcaagcgttt t                                               21

<210> SEQ ID NO 38
<211> LENGTH: 22
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: P4-3a

<400> SEQUENCE: 38
aggcatgttt cgaattgtac tt                                              22

<210> SEQ ID NO 39
<211> LENGTH: 23
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: P4-3b

<400> SEQUENCE: 39
aactttattc cctgctacac agc                                             23

<210> SEQ ID NO 40
<211> LENGTH: 30
<212> TYPE: DNA
<213> ORGANISM: Artificial Sequence
<220> FEATURE:
```

```
<223> OTHER INFORMATION: Synthetic Primer
<220> FEATURE:
<221> NAME/KEY: misc_feature
<223> OTHER INFORMATION: Long fragment PCR specific forward primer

<400> SEQUENCE: 40
caaacttcca actttcccgt caccttcact                                        30

<210> SEQ ID NO 41
<211> LENGTH: 42
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<223> OTHER INFORMATION: Long fragment PCR specific reverse primer

<400> SEQUENCE: 41
ccgcgggtca ccgagcagaa agcccttcct cccaagttag aa                          42

<210> SEQ ID NO 42
<211> LENGTH: 20
<212> TYPE: DNA
<213> ORGANISM: Artificial Sequence
<220> FEATURE:
<223> OTHER INFORMATION: Synthetic Primer

<400> SEQUENCE: 42
ctctctcacc attccttcag                                                   20

<210> SEQ ID NO 43
<211> LENGTH: 20
<212> TYPE: DNA
<213> ORGANISM: Artificial Sequence
<220> FEATURE:
<223> OTHER INFORMATION: Synthetic Primer

<400> SEQUENCE: 43
agcctaacca aacataacga                                                   20

<210> SEQ ID NO 44
<211> LENGTH: 14
<212> TYPE: PRT
<213> ORGANISM: Oryza sativa
<220> FEATURE:
<221> NAME/KEY: DOMAIN
<222> LOCATION: (1)..(14)
<223> OTHER INFORMATION: Heme binding domain of CYP81A5

<400> SEQUENCE: 44

Phe Gly Met Gly Arg Arg Cys Pro Gly Glu Thr Leu Ala
 1               5                  10

<210> SEQ ID NO 45
<211> LENGTH: 14
<212> TYPE: PRT
<213> ORGANISM: Oryza sativa
<220> FEATURE:
<221> NAME/KEY: DOMAIN
<222> LOCATION: (1)..(14)
<223> OTHER INFORMATION: Heme binding domain for CYP81A7
```

```
<400> SEQUENCE: 45

Phe Gly Met Gly Arg Arg Lys Cys Pro Gly Glu Thr Met Ala
1               5                   10

<210> SEQ ID NO 46
<211> LENGTH: 14
<212> TYPE: PRT
<213> ORGANISM: Oryza sativa
<220> FEATURE:
<221> NAME/KEY: DOMAIN
<222> LOCATION: (1)..(14)
<223> OTHER INFORMATION: Heme binding domain for CYP81A8

<400> SEQUENCE: 46

Phe Gly Met Gly Arg Arg Arg Cys Pro Gly Glu Met Leu Ala
1               5                   10

<210> SEQ ID NO 47
<211> LENGTH: 18
<212> TYPE: DNA
<213> ORGANISM: Artificial Sequence
<220> FEATURE:
<223> OTHER INFORMATION: Synthetic Primer

<400> SEQUENCE: 47
gcaggaacag agacaacc                                            18

<210> SEQ ID NO 48
<211> LENGTH: 18
<212> TYPE: DNA
<213> ORGANISM: Artificial Sequence
<220> FEATURE:
<223> OTHER INFORMATION: Synthetic Primer

<400> SEQUENCE: 48
cacctccgcc tccccatc                                            18
```